United States Patent
Douglas et al.

(10) Patent No.: US 11,583,501 B1
(45) Date of Patent: Feb. 21, 2023

(54) METHOD AND APPARATUS FOR 3D PRINTING A PRECISION PHARMACOLOGIC DOSING REGIMEN

(71) Applicants: Robert Edwin Douglas, Winter Park, FL (US); David Byron Douglas, Winter Park, FL (US); Kathleen Mary Douglas, Winter Park, FL (US)

(72) Inventors: Robert Edwin Douglas, Winter Park, FL (US); David Byron Douglas, Winter Park, FL (US); Kathleen Mary Douglas, Winter Park, FL (US)

(*) Notice: Subject to any disclaimer, the term of this patent is extended or adjusted under 35 U.S.C. 154(b) by 0 days.

(21) Appl. No.: 17/327,740

(22) Filed: May 23, 2021

Related U.S. Application Data

(63) Continuation-in-part of application No. 17/138,821, filed on Dec. 30, 2020, now Pat. No. 11,042,980, which is a continuation-in-part of application No. 16/939,192, filed on Jul. 27, 2020, now abandoned.

(60) Provisional application No. 62/956,330, filed on Jan. 2, 2020, provisional application No. 62/957,300, filed on Jan. 5, 2020.

(51) Int. Cl.
| | |
|---|---|
| *A61K 9/20* | (2006.01) |
| *A61J 3/06* | (2006.01) |
| *B33Y 50/00* | (2015.01) |
| *G06T 7/10* | (2017.01) |
| *B33Y 80/00* | (2015.01) |
| *A23P 20/20* | (2016.01) |
| *B33Y 10/00* | (2015.01) |
| *A23L 9/10* | (2016.01) |
| *G06T 7/00* | (2017.01) |
| *A23P 20/25* | (2016.01) |

(52) U.S. Cl.
CPC .............. *A61K 9/2095* (2013.01); *A23L 9/10* (2016.08); *A23P 20/20* (2016.08); *A61J 3/06* (2013.01); *B33Y 10/00* (2014.12); *B33Y 50/00* (2014.12); *B33Y 80/00* (2014.12); *G06T 7/0012* (2013.01); *G06T 7/10* (2017.01); *A23P 2020/253* (2016.08); *A23V 2002/00* (2013.01); *G06T 2207/20112* (2013.01)

(58) Field of Classification Search
None
See application file for complete search history.

(56) References Cited

U.S. PATENT DOCUMENTS

| | | | | |
|---|---|---|---|---|
| 2005/0233000 A1* | 10/2005 | Figueroa | .............. | A61K 9/7007 424/489 |
| 2019/0080459 A1* | 3/2019 | Lachaine | ............. | A61N 5/1049 |
| 2019/0374471 A1* | 12/2019 | Basit | ........ | A61K 9/205 |
| 2020/0321123 A1* | 10/2020 | Neumann | ............... | G16H 50/20 |
| 2021/0038512 A1* | 2/2021 | Cetinkaya | ................ | G06N 3/08 |
| 2021/0146105 A1* | 5/2021 | Lee | ........ | B33Y 30/00 |

(Continued)

FOREIGN PATENT DOCUMENTS

| | | | | |
|---|---|---|---|---|
| DE | 60210650 T2 * | 1/2007 | ........... | A61K 9/2095 |

*Primary Examiner* — James A Thompson

(57) ABSTRACT

This patent includes a method for utilizing imaging biomarkers to improve pharmacologic dosing strategies. Specifically, biomarker specific CT and MM examination protocols are disclosed. Dose adjustments based on imaging biomarkers are discussed. Longitudinal analysis of imaging biomarkers is disclosed assess effectiveness of pharmacotherapy and dosing strategies thereof. Finally, manufacturing of a combination pill with day-to-day variations of drug quantities is disclosed.

20 Claims, 24 Drawing Sheets

(56) References Cited

U.S. PATENT DOCUMENTS

2021/0169809 A1* 6/2021 Albed Alhnan ..... A61K 9/2072
2022/0084195 A1* 3/2022 Alberich Bayarri ... G16H 30/40

* cited by examiner

SLICE-BY-SLICE BASED CT RADIATION DOSING STRATEGY

Determine the slice location of the imaging biomarkers of interest (e.g., via scout image, via external landmarks, via very low dose CT images)
500

Determine the minimum quality of the image (e.g., spatial resolution, contrast resolution, noise, etc.) for each imaging biomarkers of interest (e.g., if the imaging biomarker is the volume of the kidney than design the protocol so that each slice has a very low radiation dose scan to derive accurate estimate of the volume of the kidney, if the imaging biomarker is an accurate Hounsfield density measurement of the parenchyma of the kidney then need a medium dose of one single CT slice for this imaging biomarker).

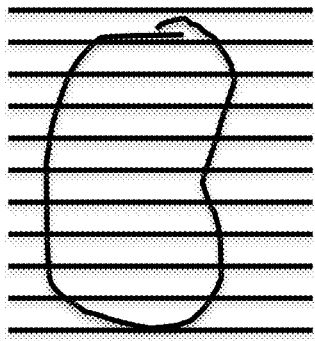

Very low dose (sufficient only to obtain volume)

Medium dose (sufficient to obtain accurate Hounsfield measurement)

Very low dose (sufficient only to obtain volume)
501

Perform the CT scan with specific acquisition parameters derived above (e.g., mAs, kVp, etc.) for each slice in the scan (e.g., do ultra-low dose CT scan of the kidney to generate precise volume as a first biomarker and do regular dose image of a single slice through the mid-kidney to understand the average Hounsfield units).
502

Figure 5

SLICE-BY-SLICE BASED MR ACQUISITION STRATEGY

---

Determine the slice location of the imaging biomarkers of interest (e.g., via scout image, via external landmarks, via MR images)
700

---

Determine the minimum quality of the image (e.g., spatial resolution, contrast resolution, noise, etc.) for each imaging biomarkers of interest (e.g., if the imaging biomarker is the volume of the kidney, then design the protocol so that each slice has a very rapid acquisition to derive accurate estimate of the volume of the kidney, if the imaging biomarker is an accurate measurement of the parenchyma of the kidney then need a different, more time consuming acquisition slice for this imaging biomarker).

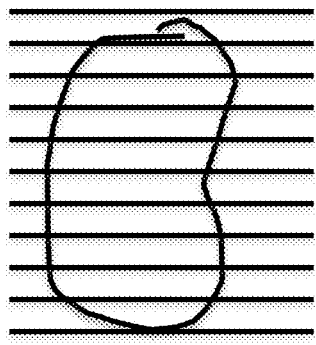

Very rapid acquisition (sufficient only to obtain volume)

Slow acquisition (sufficient to obtain accurate measurement)

Very rapid acquisition (sufficient only to obtain volume)
701

---

Perform the MRI scan with specific acquisition parameters derived above for each slice in the scan
702

Figure 7

QUALITATIVE METHOD TO TEST WHETHER AN IMAGING BIOMARKER IS RESPONSIVE TO PHARMACOTHERAPY

Determine a pathological condition (e.g., idiopathic pulmonary fibrosis) and at least one associated imaging biomarker (i.e., imaging feature that correlated with the pathological condition, such as honeycombing)
1100

Perform baseline imaging examination optimized for the at least one associated imaging biomarker
1101

Determine health status (aka, subjective severity scoring system) of imaging biomarker in the baseline imaging examination
1102

Implement pharmacotherapy
1103

Perform follow up imaging examination optimized for the at least one associated imaging biomarker
1104

Determine health status (e.g., subjective severity scoring system) of imaging biomarker in the follow up imaging examination
1105

Compare the interval change health status in between the baseline examination and the follow up examination (e.g., mild progression) with the interval change in time period (e.g., 5 years) to determine whether the pharmacotherapy is responsive to therapy (e.g., slower than normal progression, normal progression, faster than normal progression)
1106

Figure 11

LONGITUDINAL ANALYSIS OF IMAGING BIOMARKERS FOR PRECISION MONITORING OF PHARMACOTHERAPY EFFECTIVENESS

|  |  | Calendar Year | | | | | |
| --- | --- | --- | --- | --- | --- | --- | --- |
|  | Calendar year | 2022 | 2023 | 2024 | 2025 | 2026 | 2027 |
|  | Chronological age | 51 | 52 | 53 | 54 | 55 | 56 |
| Imaging biomarker | Health status of kidneys | 51 | 52 | 53 | 54 | 55 | 56 |
|  | Health status of pancreas | 51 | 52 | 53 | 54 | 55 | 56 |
|  | Health status of coronary artery calcifications | 60 | 60 | 60 | 60 | 60 | 61 |
|  | Health status of honeycombing | Mild | Mild | Mild | Mild | Mild | Mild |

Figure 12

DELIVERING SYSTEM OF THE HEALTH STATUS OF IMAGING BIOMARKERS TO THE HEALTH CARE PROFESSIONAL OR PATIENT

RADIOLOGY REPORT

| PATIENT CHRONOLOGICAL AGE: 50.1 ||
|---|---|
| IMAGING BIOMARKER | BIOMARKER AGE |
| HEART | 48.5 |
| LUNGS | 49.0 |
| LIVER | 45.1 |
| PANCREAS | 46.8 |
| ADRENAL GLANDS | 49.0 |
| KIDNEYS | 49.5 |

Figure 13

IMAGE-GUIDED MEDICATION PRIORITIZATION STRATEGY

Perform an imaging examination wherein the field of view includes at least one imaging biomarker
1400

↓

Determine the expected rate of progression of at least one imaging biomarker
1401

↓

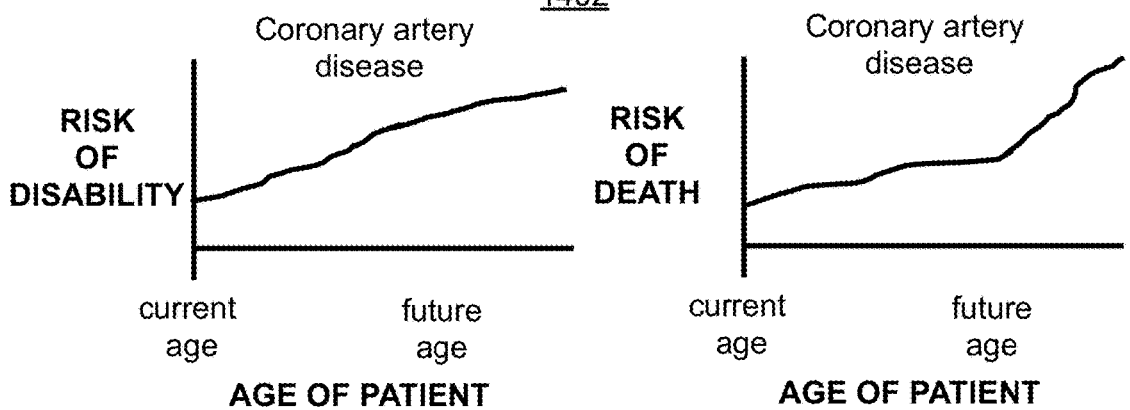

Plot the expected rate of progression of each imaging biomarker over time
1402

↓

Determine the condition that is linked to at least one imaging biomarker that is most threatening to the patient
1403

↓

Analyze metadata for other factors related to pharmacologic regimen
1404

↓

Design a pharmacologic regimen to prioritize conditions that are most threatening to the patient (e.g., maximum pharmacologic therapy to for blood pressure control for aneurysm patients to halt progression) 1405

Figure 14

A MULTI-COMPARTMENT 3D PRINTED PILL

A MULTI-COMPARTMENT, MULTI-DRUG 3D PRINTED PILL

A MULTI-COMPARTMENT, MULTI-DRUG 3D PRINTED PILL
WITH VARIABLE MEDICATION DOSES

A MULTI-COMPARTMENT, MULTI-DRUG 3D PRINTED PILL
WITH VARIABLE MATERIALS USED IN PILL COMPOSITION

METHOD AND APPARATUS FOR 3D PRINTING A PRECISION PHARMACOLOGIC DOSING REGIMEN

CROSS REFERENCES TO RELATED APPLICATIONS

This patent application is a continuation of U.S. patent application Ser. No. 17/138,821, which is a continuation in part of U.S. patent application Ser. No. 16/939,192 filed on 2020 Jul. 27, which claimed the benefit of U.S. provisional application No. 62/956,330 filed on 2 Jan. 2020 and U.S. provisional application 62/957,300 filed on 5 Jan. 2020.

TECHNICAL FIELD

This patent application applies to the field of pharmacology.

BACKGROUND

Pharmacology is a useful practice within medicine.

SUMMARY

All examples, aspects and features mentioned in this document can be combined in any technically possible way.

This disclosure improved pharmacologic dosing through the determination and manufacturing of exact doses of radiopharmaceuticals. The preferred embodiment comprises analyzing a medical imaging examination wherein said medical imaging examination comprises at least one imaging biomarker; and determining a dose of a pharmaceutical based on said at least one imaging biomarker.

Some embodiments comprise wherein said at least one imaging biomarker comprises at least one of the group consisting of: categorical variable(s); ordinal variable(s); binary variable(s); and continuous variable(s). Some embodiments comprise wherein said at least one imaging biomarker is characterized via an artificial intelligence algorithm.

Some embodiments comprise wherein said dose of said pharmaceutical is adjusted via an artificial intelligence algorithm. Some embodiments comprise adjusting said dose based on activities of daily living.

Some embodiments comprise wherein said at least one imaging biomarker comprises at least one a pathologic condition. For example, a bone mineral density metric on a DEXA scan with a value indicating osteoporosis indicates a pathologic condition.

Some embodiments comprise wherein said at least one imaging biomarker comprises quantitative data based on a normal anatomic structure.

Some embodiments comprise wherein said at least one imaging biomarker comprises a binary variable used to characterize an anatomic structure as either normal or as abnormal.

Some embodiments comprise performing analysis of a 3D dataset from a medical imaging examination to extract said at least one imaging biomarker wherein said image analysis comprises at least one of the group consisting of: performing segmentation of said 3D dataset to generate a segmented structure; determining a linear size of a segmented structure; determining a number of segmented structures within an organ; determining a predicted age of an organ; determining a ratio of a first segmented structure to a second segmented structure; determining volume of a segmented structure; determining a shape of a segmented structure; determining a density of a segmented structure; determining a physiologic parameter of a segmented structure; determining an enhancement pattern of a segmented structure; determining a standardized uptake value of a segmented structure; determining a surface area of a segmented structure; and performing a radiomic analysis of a segmented structure.

Some embodiments comprise utilizing a dedicated medical imaging examination protocol for pharmacologic dosing strategy.

Some embodiments comprise wherein analyzing an imaging biomarker longitudinally over at least two different imaging examinations to determine effectiveness of pharmacotherapy.

Some embodiments comprise wherein adjusting said dose of said pharmaceutical based on interval change of said at least one imaging biomarker.

Some embodiments comprise: generating a health status of said at least one imaging biomarker; and utilizing said health status of said imaging biomarker for at least one of the group consisting of: selection of pharmaceutical; and adjusting said dose of said pharmaceutical.

Some embodiments comprise: predicting a time of an adverse health event; and adjusting said dose of said pharmaceutical based on predicting said time of said adverse health event.

Some embodiments comprise adjusting a dose of a pharmaceutical based on at least one of the group consisting of: a photograph from a dermatologic finding; data collected from an internet of things; and a laboratory finding.

Some embodiments comprise wherein at least one of the group consisting of: manufacturing said dose; and mixing said dose with a food item or a drink item.

Some embodiments comprise predicting a pain level based on said imaging biomarker.

Some embodiments comprise wherein said medical imaging examination comprises an imaging biomarker specific protocol wherein said imaging biomarker specific protocol comprises at least one of the group consisting of: a CT scan wherein said CT scan comprises a low dose scan with a contrast resolution sufficient to delineate the boundaries of the organs; and a MM scan wherein said MM scan comprises a rapid acquisition examination with contrast resolution sufficient to delineate the boundaries of the organs.

Some embodiments comprise a non-transitory computer readable information storage medium having computer-executable instructions which, when executed by a computing device, cause the computing device to perform the operations of analyzing a medical imaging examination wherein said medical imaging examination comprises at least one imaging biomarker; and determining a dose of a pharmaceutical based on said at least one imaging biomarker.

Some embodiments comprise a 3D printer loaded with a first drug and a second drug wherein said 3D printer is configured to receive instructions to combine a predetermined first dose of said first drug and a predetermined second dose of said second drug. Some embodiments comprise wherein said 3D printer is located on a centrifuge in space, as disclosed in U.S. patent application Ser. No. 15/679,329, SIMULATED GRAVITY DEVICE, which is incorporated by reference in its entirety.

The preferred embodiment is a method of determining a precise dosing regimen of at least one pharmaceutical comprising: determining the pathologic condition of a patient that needs treatment with at least one pharmaceutical; collecting a set of metadata on the patient; performing a medical imaging examination containing at least one anatomic structure; analyzing the at least one anatomic structure within the medical imaging examination to determine at least one quantitative metric on the at least one anatomic structure; importing both the set of metadata on the patient and the at least one quantitative metric on the at least one anatomic structure into an analytical model; and performing the analytical model to determine a precise dosing regimen of at least one pharmaceutical. A pharmacologic dose is therefore adjusted based on an imaging finding.

Some of the techniques in this patent are performed by utilizing techniques described in: U.S. patent application Ser. No. 15/878,463, Interactive 3D cursor for use in medical imaging; U.S. patent application Ser. No. 16/010,925, Interactive placement of a 3D digital representation of a surgical device or anatomic feature into a 3D radiologic image for pre-operative planning; U.S. patent application Ser. No. 15/904,092, Processing 3D medical images to enhance visualization; U.S. patent application Ser. No. 15/949,202, Smart operating room equipped with smart surgical devices; U.S. Pat. No. 9,473,766, Method and apparatus for three dimensional viewing of images; U.S. Pat. No. 9,615,806, Method and apparatus for creation and display of artifact corrected three dimensional (3D) volumetric data from biplane fluoroscopic image acquisition; U.S. patent Ser. No. 14/644,489, Method and apparatus for creation and display of artifact corrected three dimensional (3D) volumetric data from biplane fluoroscopic image acquisition; U.S. Pat. No. 9,980,691, Method and apparatus for three dimensional viewing of images; U.S. Pat. No. 9,349,183, Method and apparatus for three dimensional viewing of images; U.S. patent application Ser. No. 16/195,251, Interactive voxel manipulation in volumetric medical imaging for virtual motion, deformable tissue, and virtual radiological dissection; U.S. patent application Ser. No. 16/509,592, Implantable markers to aid surgical operations; U.S. patent application Ser. No. 16/524,275, Using geo-registered tools to manipulate three-dimensional medical images; PCT/US19/478, A virtual tool kit for radiologists; U.S. patent application Ser. No. 16/563,985, A method and apparatus for the interaction of virtual tools and geo-registered tools; U.S. patent application Ser. No. 16/594,139, Method and apparatus for performing 3D imaging examinations of a structure under different configurations and analyzing morphologic changes; U.S. patent application Ser. No. 16/683,256, Method and apparatus for performing 3D imaging examinations of a structure under different configurations and analyzing morphologic changes; U.S. patent application Ser. No. 16/703,629, Radiologist-assisted machine learning with volume-subtending 3D cursor; PCT/US19/239, Radiologist-assisted machine learning with interactive, volume-subtending 3D cursor; U.S. provisional application No. 62/843,612, A method of creating a computer-generated patient specific image; U.S. provisional application No. 62/846,770, A method of prioritized volume rendering to improve visualization of prioritized items within a 3D volume; U.S. provisional application No. 62/850,002, A method of creating an artificial intelligence generated differential diagnosis and management recommendation tool boxes during medical personnel analysis and reporting; U.S. patent application Ser. No. 16/654,047, A method to modify imaging protocols in real time through implementation of artificial intelligence; U.S. provisional application No. 62/856,185, A method of image manipulation based on eye tracking; U.S. patent application Ser. No. 16/506,073, A method for illustrating direction of blood flow via pointers; U.S. patent application No. 62/906,125, A method and apparatus for stereoscopic rendering of mobile fluids; and, U.S. patent application No. 62/939,685, Method and apparatus for development of an organ-specific coordinate system.

In the preferred embodiment, a total body scan such as a DEXA scan, total body MRI or low dose total body CT scan is performed. The variable body composition (bone, fat, muscle, organ size, pathologies, etc.) would be quantified. The imaging examination would be reviewed for pathology for screening purposes. For each drug, the quantitative and qualitative data from the medical imaging examination is inputted into an analytical model to determine the precise dose for a particular disease. Each drug would be delivered at the precise dose. The result would be lower cost through saving lower doses when available and lower side effects. In alternative embodiments, the protocol could be modified to improve ability to characterize certain imaging biomarkers. For example, if the imaging biomarker is the liver volume and this does not require good contrast resolution to see details of the liver itself, than use extreme low radiation dose. The physician can order a scan with protocol stating, "undergoing pharmacotherapy for coronary artery atherosclerotic disease, carotid artery atherosclerotic disease and renal parenchyma disease, please perform imaging biomarker for pharmacotherapy protocol." Since the imaging biomarkers are coronary artery narrowing, carotid artery narrowing, and renal cortex thickness, the protocol is optimized to do arterial phase for carotid and coronary artery fields of view and renal cortical phase for renal cortex.

In some embodiments, the method further comprises designing CT scan protocols to optimize visualization of imaging biomarkers for pharmacologic dosing strategy. This method comprises determining the most useful imaging biomarkers (e.g., coronary artery disease and renal health) related to pathological conditions (e.g., coronary artery disease kidney disease). Also, determine the field of view (or fields of view) of the examination. Also, adjust the radiation dose to optimizing visualization of the imaging biomarker (e.g., if the imaging biomarker is the liver volume and this does not require good contrast resolution to see details of the liver itself, than use extreme low radiation dose). Also, adjust the contrast dose and timing to optimize visualization of the imaging biomarker (e.g., if the imaging biomarkers are coronary artery narrowing, carotid artery narrowing, and renal cortex thickness, then do arterial phase for carotid and coronary artery fields of view and renal cortical phase for renal cortex). Also, perform appropriate post-processing techniques to ready the images for quantitative and qualitative interpretation of the imaging biomarker.

In some embodiments, the method further comprises providing a specialized slice-by-slice based CT radiation dosing strategy for image acquisition for optimization of imaging biomarkers. This method comprises determining the slice location of the imaging biomarkers of interest (e.g., via scout image, via external landmarks, via very low dose CT images). Also, determine the minimum quality of the image (e.g., spatial resolution, contrast resolution, etc.) for each imaging biomarkers of interest (e.g., if the imaging biomarker is the volume of the liver than design the protocol so that each slice has a very low radiation dose scan to derive accurate estimate of the volume of the liver, if the imaging biomarker is an accurate Hounsfield density measurement of the parenchyma of the liver then need a medium dose of one single CT slice for this imaging biomarker). Note that this protocol teaches the opposite of current CT protocols, which are designed specifically for the purpose of providing similarly optimized image quality over contiguous slices. In contrast, this technique is designed to have sub-optimal image quality (e.g., below the quality level for the diagnostic radiologist) on slices containing imaging biomarkers which only need sub-optimal image quality. A first example imaging biomarker is the kidney volume. Since the kidney is surrounded by fat, which has an average Hounsfield units of approximately −100 and the kidney has an average Hounsfield unit of approximately 40, an extremely low dose CT image (e.g., very low mA and very low kVp) is used to provide only enough contrast to distinguish the fat from the renal parenchyma. A second example imaging biomarker is the average Hounsfield units for the renal parenchyma of the mid renal slice. To achieve this, a routine dose CT scan is performed for a single slice of the kidney. Thus, the slice-by-slice based CT radiation dosing strategy can yield one single slice with a medium dose and one set of slices with an extremely low dose; thus, two drastically different doses of the same organ can be performed. Then, perform the CT scan with specific acquisition parameters derived above (e.g., mAs, kVp, etc.) for each slice in the scan (e.g., do ultra-low dose CT scan of the kidney to generate precise volume as a first biomarker and do regular dose image of a single slice through the mid-kidney to understand the average Hounsfield units).

In some embodiments, the method further comprises designing an MRI protocol used for pharmacologic dosing strategy. This method comprises determining the most useful imaging biomarkers (e.g., coronary artery disease and renal health) related to pathological conditions (e.g., coronary artery disease kidney disease). Next, determine the field of view (or fields of view) of the examination. Next, adjust the MM sequences to optimizing visualization of the imaging biomarker (e.g., if the imaging biomarker is the liver volume and this does not require good contrast resolution to see details of the liver itself, than use rapid sequences, such as single shot fast spin echo). Next, adjust the contrast dose and timing to optimize visualization of the imaging biomarker (e.g., if the imaging biomarkers is renal cortex thickness, then do a T1-weighted post-contrast sequence renal cortical phase for renal cortex). Next, perform appropriate post-processing techniques to ready the images for quantitative and qualitative interpretation of the imaging biomarker.

In some embodiments, the method further comprises providing a specialized slice-by-slice based MR acquisition strategy for image acquisition for optimization of imaging biomarkers. This method comprises determining the slice location of the imaging biomarkers of interest (e.g., via scout image, via external landmarks, via very low dose MR images). Also, determine the minimum quality of the image (e.g., spatial resolution, contrast resolution, etc.) for each imaging biomarkers of interest (e.g., if the imaging biomarker is the volume of the liver than design the protocol so that each slice is acquired rapidly with high spatial resolution and low contrast resolution to derive accurate estimate of the volume of the liver, if the imaging biomarker is an accurate tissue measurement of the parenchyma of the liver then need a long acquisition of a single MR slice for this imaging biomarker). Note that this protocol teaches the opposite of current MR protocols, which are designed specifically for the purpose of providing similarly optimized image quality over contiguous slices. In contrast, this technique is designed to have sub-optimal image quality (e.g., below the quality level for the diagnostic radiologist) on slices containing imaging biomarkers which only need sub-optimal image quality. A first example imaging biomarker is the kidney volume. Since the kidney is surrounded by fat, which has vastly different chemical properties than renal parenchyma, an extremely rapid acquisition MR is used to provide only enough contrast to distinguish the fat from the renal parenchyma. A second example imaging biomarker is the average tissue measurement (e.g., ADC map measurement) for the renal parenchyma of the mid renal slice. To achieve this, lengthy MRI sequence is performed for a single slice of the kidney. Thus, the slice-by-slice based MR strategy can yield one single slice of high quality and one set of slices with an extremely low quality; thus, two drastically different image quality scans of the same organ can be performed. Then, perform the MRI scan with specific acquisition parameters derived above for each slice in the scan.

In some implementations, a variety of inputs are utilized in determining the precise dosing regimen. It is intended in this embodiment that a variety of inputs will be used to supplement the aforementioned imaging biomarkers with a labeled health score (or BIOMARKER AGE). These inputs include, but are not limited to, the following: laboratory data; medical history data; and interval changes in an anatomical structure over multiple time points while taking a particular medicine(s). Together, analysis of imaging biomarkers and other inputs yields a more precise pharmacologic dosing.

The preferred embodiment for precision pharmacologic dosing is through the intermediate step of labeling imaging biomarkers with a health score (e.g., biomarker age). In this method, first build a normative dataset for each imaging biomarker in an imaging examination (e.g., maximum percentage stenosis of the left anterior descending artery, etc.). Next, perform an imaging examination including at least one imaging biomarker (e.g., maximum percentage stenosis of the left anterior descending artery, etc.), but preferably perform a whole body or near whole body cross-sectional imaging examination (e.g., CT or MRI). Next is an option to isolate imaging biomarker (e.g., perform segmentation, 3D cursor, etc.). This can be done through segmentation and filtering. This can be performed prior to, during or after a patient is treated with a medication regimen. This is useful because understanding the health status of various imaging biomarkers can be useful in determining a pharmacologic dosing regimen.

The preferred embodiment is to use the weighting factors associated with the developed imaging biomarkers to determine precision therapy. At this juncture, the set of imaging biomarkers have been assigned a health status (e.g., biomarker age) based on the appearance of the imaging biomarker as compared to the normative dataset. Next, establish a weighting factor for each imaging biomarker. The weighting factors should be correlated to the pathology proportionately. For example, assume the health status of an organ could be reliably characterized by two known imaging biomarkers, with each imaging biomarker being of equal importance. To further teach this, consider that the kidneys a 50% weight could be allocated based on the volume and a 50% weight could be allocated based on the average Hounsfield Unit density of the mid-slice on a non-contrast examination and together these two imaging biomarkers would be a reliable assessment of the health status of the kidneys. Next, determine biomarker age based on imaging biomarkers and associated weighting factors. In the preferred embodiment, an artificial intelligence/machine learning algorithm could be utilized to predict the health status (e.g., biomarker age). Next, perform precise pharmacologic dosing regimen (e.g., based on desired goal of pharmacotherapy, known impacts of pharmacotherapy on biomarkers, biomarker age, other metadata, etc.). In the preferred embodiment, a machine learning approach which utilizes a database of past data could be implemented to determine the pharmacologic regimen that would minimize progression of imaging biomarkers over time and maximizes longevity and wellness. Other mathematical approaches (e.g., statistical processes for risk prediction, such as linear regression or other advanced models) could also be implemented to achieve these goals. In practice, two options could be performed. First, the physician could decide to have the process to be completely automated wherein the artificial intelligence algorithm analyzes the metadata (e.g., age, labs, medical history, physical examination) and the imaging biomarkers with their associated health status and then the artificial intelligence algorithm determines a medication regimen on its own with precise doses of each medicine. Alternatively, the physician could decide to prescribe the medication regimen and allow the artificial intelligence algorithm to determine the doses. For example, an initial dose is prescribed and then a corrective factor is applied to determine the optimal dose. For example, a physician may prescribe 100 mg of doxycycline and then a corrective factor is implemented based on imaging biomarkers (such as the liver volume, liver density, kidney volume, kidney cortical thickness, bone mineral density or other imaging biomarkers) and a final dose of 81.7 mg is prescribed. An option is for the physician to review the AI prescription and perform an adjudication process, such as is described in U.S. patent application Ser. No. 16/703,629.

Some embodiments comprise methods to test whether a quantitative imaging biomarker is responsive to pharmacotherapy. This method comprises determining a pathological condition (e.g., coronary artery disease) and at least one associated imaging biomarker (e.g., imaging feature that is correlated with the pathological condition, such as calcium score). Other examples include the density of a particular structure. For example, in patients with hemochromatosis, iron accumulates in the liver. A 3D cursor can be used, as is described in U.S. patent application Ser. No. 15/878,463, Interactive 3D cursor for use in medical imaging to assess iron quantities. Next, perform baseline imaging examination optimized for the at least one associated imaging biomarker. Next, determine health status (e.g., biomarker age) of imaging biomarker in the baseline imaging examination. Next, implement pharmacotherapy. Next, perform follow up imaging examination optimized for the at least one associated imaging biomarker. Next, determine health status (e.g., biomarker age) of imaging biomarker in the follow up imaging examination. Next, compare the health status at the baseline imaging examination with the health status at the follow up imaging examination to determine interval change in health status. Next, compare the interval change health status in between the baseline examination and the follow up examination (e.g., 1 year progression) with the interval change in time period between the scans (e.g., 5 years progression) to determine whether the pharmacotherapy is responsive to therapy. For example, if the coronary artery calcium score progressed 1 years (of severity/danger) over 5 years of time period that has passed, that would be considered relatively effective whereas if the coronary artery calcium score progressed 13 years (of severity/danger) over 5 years of time period that has passed, that would be considered relatively ineffective. Thus, this method provides studying imaging biomarkers to determine effectiveness of pharmacotherapy.

In some embodiments, the method further comprises analyzing the at least one anatomic structure within the medical imaging examination to determine at least one qualitative metric on the at least one anatomic structure. This method comprises determining a pathological condition (e.g., idiopathic pulmonary fibrosis) and at least one associated imaging biomarker (i.e., imaging feature that correlated with the pathological condition, such as honeycombing). Next, perform baseline imaging examination optimized for the at least one associated imaging biomarker. Next, determine health status (aka, subjective severity scoring system) of imaging biomarker in the baseline imaging examination. Next, implement pharmacotherapy. Next, perform follow up imaging examination optimized for the at least one associated imaging biomarker. Next determine health status (e.g., subjective severity scoring system) of imaging biomarker in the follow up imaging examination. Next, compare the health status at the baseline imaging examination with the health status at the follow up imaging examination to determine interval change in health status. For example, compare the interval change health status in between the baseline examination and the follow up examination (e.g., mild progression) with the interval change in time period (e.g., 5 years) to determine whether the pharmacotherapy is responsive to therapy (e.g., slower than normal progression, normal progression, faster than normal progression).

Some embodiments comprise a longitudinal analysis of imaging biomarkers for precision monitoring of pharmacotherapy effectiveness. For example, a table can be presented with the imaging biomarkers in rows and the columns in years in an annual imaging examination model. The health status of each anatomic imaging biomarker (e.g., estimated age) can be tracked over time. Additionally, the health status of each pathologic finding (e.g., severity of honeycombing) can be tracked over time and plotted.

In some embodiments, the method further comprises analyzing at least one surgical device in the analytical model to determine a precise dosing regimen of at least one pharmaceutical. For example, give ~10% higher dose of blood thinner if a cardiac stent is present. For example, give ~5% less dose of blood thinner if an IVC filter is present. Precise dosing strategies would be determined by various models.

In some implementations, the method comprises delivering the health status of various imaging biomarkers to the health care professional or patient. For example, this can be in the form of a table with the imaging biomarker presented in a manner which is easily interpreted by the physician or patient.

In some implementations, an image-guided medication prioritization strategy is implemented. First, perform an imaging examination wherein the field of view includes at least one imaging biomarker (e.g., optimize imaging examination for imaging biomarker, perform routine radiologic interpretation of the examination for incidental pathologies, quantitative interpretation of imaging biomarker, qualitative interpretation of imaging biomarker, etc.). Then, determine the expected rate of progression of at least one imaging biomarker (e.g., use actual patient data compare interval change of imaging biomarker over multiple examinations, use repository of population data to obtain expected rate of progression, combination thereof, etc.). Then, plot the expected rate of progression of each imaging biomarker over time. Then, determine the condition (i.e., that is linked to at least one imaging biomarker) that is most threatening to the patient (e.g., the condition that is predicted to cause symptoms, disability or death at the youngest patient age, etc.).

Then, analyze metadata for other factors related to pharmacologic regimen (e.g., labs, physical examination, medication compliance, etc.).

In some implementations, a new set of contraindications (or cautions) for giving a particular medication is established. For example, if the liver appears to have an age that is more advanced (e.g., # years more advanced, or # of standard deviations more advanced, etc.) than the patient's chronological age, then action can be taken (e.g., decrease the dose of hepatotoxic drugs commensurately). For example, if the kidneys appear to have an age that is more advanced (e.g., # years more advanced, or # of standard deviations more advanced, etc.) than the patient's chronological age, then action can be taken (e.g., decrease the dose of nephrotoxic drugs commensurately). For example, if the bones appear to be more demineralized (e.g., # years more advanced, or # of standard deviations more advanced, etc.) than the actual patient age, then action can be taken (e.g., decrease the dose of drugs that adversely effect bone mineral density commensurately).

In some implementations, the interrelationship between medication regimens and anatomical features can be modeled to improve understanding of side effects. For example, assume patients on medication A have typical aging of all imaging biomarkers. Assume patients on medication B have typical aging of all imaging biomarkers. Assume patients on both medication A and medication B consistently had accelerated aging of a particular imaging biomarker #N. Such a finding would be concern for a deleterious medication interaction.

Some implementations include precision manufacturing of a pharmaceutical dose. First, determine the precision pharmacologic regimen. Then, assemble all of the medications in the precision pharmacologic regimen. Then, determine if there are known medication interactions (e.g., medications that should not be combined in the same pill). Then, determine the optimized combination of medications to be in a single pill (e.g., those medications that are best to be taken on an empty stomach are combined into a first pill, those medications that are best to be taken with water are combined to a second pill, those medications that are best to be taken with food are combined into a third pill, etc.). Then, determine the best way to label the pills (e.g., specific color of pill for specific purpose, orange to be taken with food, blue to be taken with water, etc.). Then, perform manufacturing (e.g., use 3D printing, tablet construction, capsule construction, capsule with variable breakdown rates yields delayed release of certain elements). In some implementations, a combined pill is specially designed for the patient, which consists of multiple medications. For example, 3D printing can be used to manufacture the precise dosing regimen as determined by the algorithm.

In some implementations, a cost model for combination pill is provided. First, determine the pharmacologic regimen. Then, determine the cost per unit dose for each medicine in the regimen. Then, determine the dose for each medicine in the regimen. Then, multiply the cost per unit dose by the precision prescribed dose for each medicine in the regimen to determine the total cost of each medicine. Then, determine the manufacturing costs (e.g., use 3D printing) per pill. Then, multiply the cost of manufacturing each pill by the number of pills in the regimen to determine the total cost.

In some implementations, a comprehensive patient care model is established. First, perform an imaging guided prioritization strategy. Then, prescribe the determined pharmacologic regimen. Then, build the combination pill (e.g., use 3D printing). Some embodiments further comprise combining multiple medications into a single combination pill. This is performed to make it easier for a patient to take multiple medications and improve compliance. Then, perform pharmacotherapy for a prescribed time period. Then, perform monitoring (e.g., labs, physical examination).

In some implementations, the medication dosing regimen would be optimized to minimize progression of the condition that is most likely to cause disability or death. A human's life span and wellness are only as good as its weakest link. For example, if a patient had an untreated abdominal aortic aneurysm, but no other critical illness, the medication regimen would be optimized to mitigate growth of the abdominal aortic aneurysm, namely through blood pressure control. For example, if a patient had a history of 80% stenosis of the left main coronary artery, the medication regimen would be optimized to slow, halt, or reverse the atherosclerotic narrowing. Therefore, the medication regimen would be focused to target the condition that poses the greatest threat to the patient.

In some implementations, a delivery system of the health status of the imaging biomarkers can be performed via reporting. The preferred embodiment would be to have all radiology reports have each major organ with a particular BIOMARKER AGE or health status. This is useful because it would be helpful to deliver this information to those whose internal organs are aging at a rate that is faster than their chronological age because it could potentially be a motivator for healthier living. In some implementations, it would be reassuring to those whose age is at or below.

In some implementations, data from one or more devices, (e.g., implantable cardiac devices, implantable spine stimulators, wearable sensors, such as heart monitors, EEG monitors, blood pressure monitors, Apple watch, the internet of things (IOT) etc.) is gathered on an individual, such as in a "big data". Such data can be time stamped and includes, but is not limited to, the following: heart rate, blood pressure, stress level, pulse oximetry, activity level (e.g., steps, rate, sleep hours, sleep quality), and other things on the human body. For example, when the person is linked in, every heartbeat from their life would be recorded and time stamped. Some data can be inputted from the patient via devices such as cell phone apps (e.g., questionnaire data to collect information such as energy level, anxiety level, depression level, subjective response to medications, etc.). Thus, qualitative and quantitative data can be inputted into "individualized big data". In some implementations, the "individualized big data" can be utilized to optimize the next medicine regimen. For example, a pharmacy locally with a 3D printer can print a combination pill individualized for a specific person based on the "individualized big data" and deliver it to the person in a rapid fashion (e.g., use drones and deliver within 1 hour or sooner). For example, if a person finds out that he/she needs to make a 5-hour long road trip, the pill may be optimized to have a mini dose of blood thinner. For example, if a person needs to go to sleep early that night, a newly manufactured pill may contain melatonin. For example, if the person is going to undergo a highly stressful event, but is at an elevated risk of a heart attack, the daily pill can include a higher dose of aspirin, rather than a baby dose of aspirin. Feedback from the user can be performed, to improve the pharmacologic regimen. Through this system, a person who utilizes sensors (e.g., apple watch, other items from the internet of things) to gather "individualized big data" to drive a precision pharmacotherapy regimen and provides feedback to the system would optimize health and wellness.

Some embodiments comprise a method, a software and an apparatus to design a pill for manufacturing. In the preferred embodiment, the pill is manufactured on a 3D printer. Some embodiments comprise using a set of patient factors to determine a first dose of a first medication and second dose of a second medication. Next, the pill contains the first dose of said first medication and said second dose of said second medication. Finally, the pill is manufactured using a 3D printer.

Some embodiments comprise wherein said set of patient factors include, but not limited to the following: a weight of a patient; a patient's gender; a patient's age; a patient's laboratory data; a patient's body mass index; and a patient's diagnosis.

Some embodiments comprise wherein said dose of said first medication and said dose of said second medication are determined by an artificial intelligence algorithm. Techniques for artificial intelligence are described in the patents incorporated by reference.

Some embodiments comprise wherein said pill comprises a multi-compartment design with at least two compartments. For example, a design includes a first compartment and a second compartment wherein said first compartment and said second compartment are different compartments.

Some embodiments comprise wherein the first compartment contains a first medication and the second compartment contain the same first medication. Some embodiments comprise placing a first portion of said first dose of said first medication in said first compartment wherein said first portion of said first dose of said first medication is released from said first compartment into a patient's gastrointestinal tract during a first time period (such as during the first 12 hours following swallowing the pill). Additionally, this embodiment includes placing a second portion of said first dose of said first medication in said second compartment wherein said second portion of said first dose of said first medication is released from said second compartment into said patient's gastrointestinal tract during a second time period (such as a time period beginning at 12 hours after swallowing the pill) wherein said second time period begins after said first time period.

Some embodiments comprise wherein said first compartment contains said first medication and said second compartment contain said second medication. Some embodiments comprise wherein when said first medication is known to interact with said second medication, placing said first medication in said first compartment wherein said first medication is released from said first compartment into a patient's gastrointestinal tract during a first time period. Additionally, this embodiment includes placing said second medication in said second compartment wherein said second medication is released from said second compartment into said patient's gastrointestinal tract during a second time period wherein said second time period begins after said first time period.

Some embodiments comprise wherein after said pill is swallowed by a patient, said first compartment delivers its content into a gastrointestinal tract of said patient over a first time period, wherein said second compartment delivers its content into said gastrointestinal tract of said patient over a second time period, and wherein said first time period is different from said second time period.

Some embodiments comprise wherein said first compartment's lining is of a made of a first material and said second compartment's lining is made of a second material, wherein said first material is different from said second material, and wherein said first material dissolves quicker in a gastrointestinal track as compared to said second material.

Some embodiments comprise wherein said first compartment's lining is thicker than said second compartment's lining and wherein said first medication is released in a gastrointestinal track slower than said second medication.

Some embodiments comprise wherein said first compartment is a first shape and said second compartment is a second shape, and wherein said first shape is different from said second shape.

Some embodiments comprise wherein said first compartment is contains a first volume and said second compartment contains a second volume, and wherein said first volume is larger than said second volume.

Some embodiments comprise wherein said first compartment is in a first position within said pill and said second compartment is in a second position within said pill, and wherein said first position is different from said second position.

Some embodiments comprise wherein said pill contains a third dose of a third medication.

Some embodiments comprise wherein said pill is integrated into an edible item printed on said 3D printer. This could be a dessert like chocolate or other edible item including food and drink. A wide range of designs including shapes and colors could be used.

Some embodiments comprise wherein said pill contains patient selected vitamins and minerals. For example, assume that an 80 year old man likes to incorporate Vitamin D, B complex, Vitamin C along with a Eliquis and Lipitor. All of these could be combined into one single pill (or edible item, as described above, such as a cube, sphere or dodecahedron).

In some embodiments, the medication is mixed with a material which controls the rate of the delivery of a medication. This could be done by having a 3D grid, a gummy substance, a substance commensurate with the delivery, or a multi-compartment design. For example, a hard portion of the gummy that is difficult to break down would deliver the medication at a slower rate than a soft, easy to break down portion of the gummy.

In some embodiments, a designer one-a-day, multicompartment pill is used. In some embodiments, wherein a 3D printer designs a barrier so that the first dose is released at a different time interval as compared to the second dose. In some embodiments, laboratory data from a patient, which includes but is not limited to the following: pH of blood; blood type; a complete blood count; blood chemistries; cholesterol; electrolytes; and others. In some embodiments, these elements can be used for dose adjustment. Additionally, the pill can be designed with a pre-determined thickness and/or material so that a particular medication is released at a predetermined time of day. For example, assume that person is giving a major speech at 3 PM. The pill could include a beta blocker or an anxiolytic and be designed with a thickness of a particular compartment to be swallowed at 7 AM, but dissolved in the early afternoon so that its peak effectiveness is during the speech. Thus, the techniques enclosed in this patent can be used to design a one-a-day pill to strategically deliver medications, vitamins and minerals over a one-day time period.

Definitions

Metadata includes, but is not limited to, gender, age, weight, genetics, or other features that describe a patient.

Analytical model includes, but is not limited to, a mathematical model, AI, ML, or other analytical models.

Medical imaging examination includes radiograph, ultrasound, computed tomography (CT), magnetic resonance imaging, nuclear medicine techniques, or other techniques. Anatomic structures include, but are not limited to the following: normal anatomy (e.g., liver), pathology (e.g., hemangioma within liver) or combinations thereof.

Surgical device includes, but is not limited to, the following: any non-naturally occurring object in the body (e.g., cardiac stent, pacemaker, orthopedic device, etc.).

Imaging biomarkers includes, but is not limited to the following: any anatomic or pathologic structure in the field of view of a medical imaging examination that can be analyzed quantitatively or qualitatively.

Quantitative analysis includes, but is not limited to, the following: volume of organ; volume of pathology; or other metrics with units such as $cm^2$, cm, $cm^3$, SUV, Hounsfield units, etc.

Qualitative metric includes location of tumor, invasion of tumor into local structure, proximity of pathology to local structure or vocabulary terms to describe disease or normal anatomy states.

Precise dosing regimen includes, but is not limited to, the following: quantity of dose; timing of dose; duration of dose.

Feedback from patient includes, but is not limited to the following: symptoms, or other metrics.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g., when executing) on the processor, operates as explained herein within the computerized device to perform all of the method embodiments and operations explained herein as embodiments of the invention. Thus, any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 illustrates a slice-by-slice based CT radiation dosing strategy.

FIG. 7 illustrates a slice-by-slice based MR acquisition strategy.

FIG. 11 illustrates qualitative method to test whether an imaging biomarker is responsive to pharmacotherapy.

FIG. 12 illustrates longitudinal analysis of imaging biomarkers for precision monitoring of pharmacotherapy effectiveness.

FIG. 13 illustrates delivering system of the health status of imaging biomarkers to the health care professional or patient.

FIG. 14 illustrates image-guided medication prioritization strategy.

21A Two types of medications in one pill wherein there is no interaction between the two medications.

21B Two types of medications in one pill wherein there is an interaction between the two medications.

21C Two types of medications in one pill wherein the medication in the first compartment is released at a different time of day as compared to the medication in the second compartment.

Figure 22A:
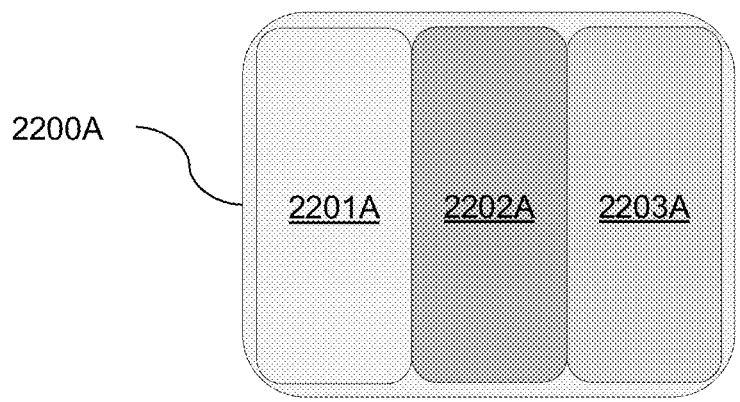

FIG. 22A illustrates a multi-compartment pill wherein there are three types of medications in one pill and wherein there is no interaction between any of the three medications.

Figure 22B:
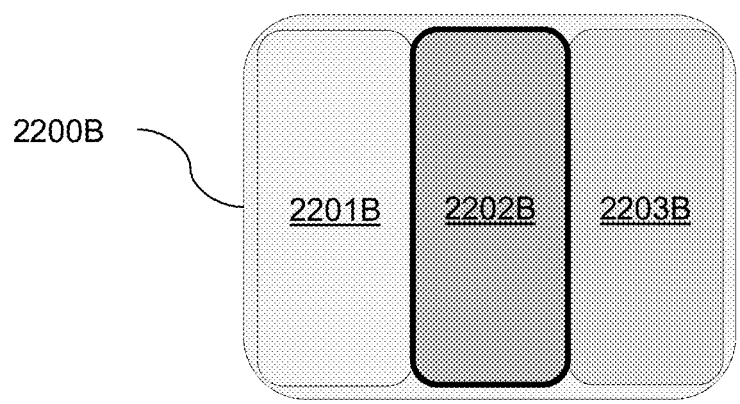

FIG. 22B illustrates a multi-compartment pill wherein there are three types of medications in one pill and wherein there is an interaction between one of the medications and the other two medications.

Figure 22C:
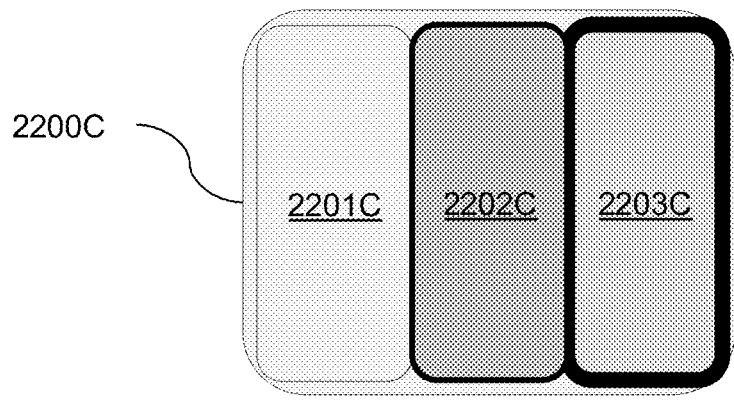

FIG. 22C illustrates a multi-compartment pill wherein there are three types of medications in one pill and wherein all three medications interact.

Figure 23A:
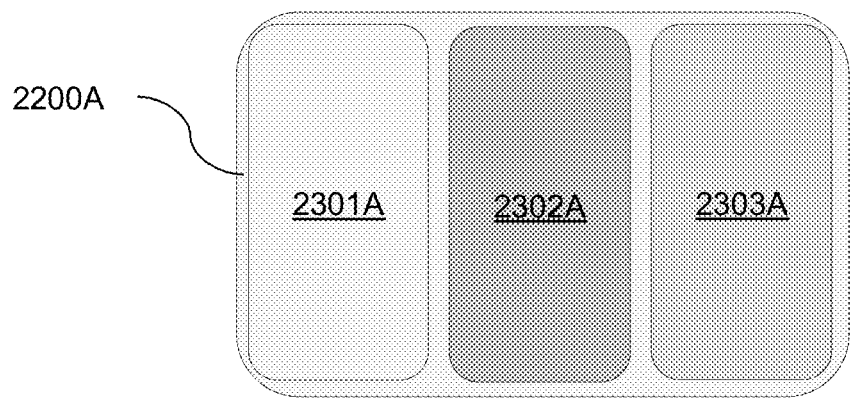

FIG. 23A illustrates a first pill with three medications with a first volume of a first medication, a second volume of a second medication, and a third volume of a third medication.

Figure 23B:
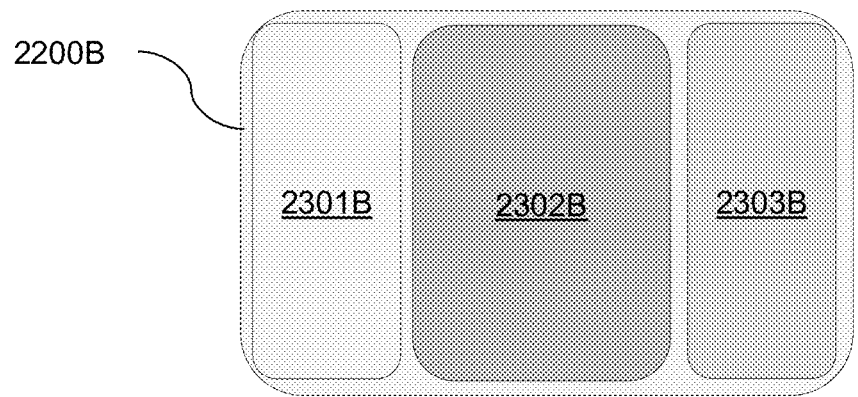

FIG. 23B illustrates a second pill with three medications with different volumes of each medicine.

Figure 24A:
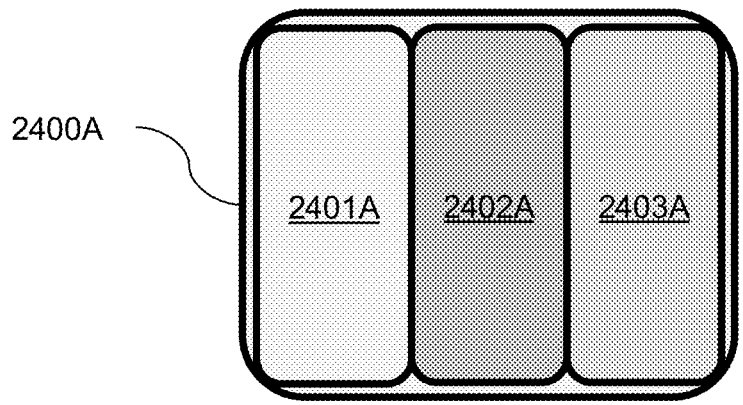

FIG. 24A illustrates a first pill with three medications, each of which are stored in a compartment made of the same material.

Figure 24B:
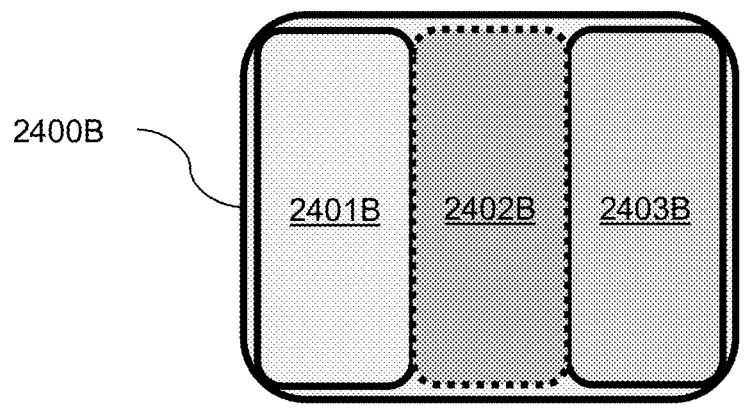

FIG. 24B illustrates a second pill with three medications wherein compartments made of different materials.

DETAILED DESCRIPTION OF FIGURES

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
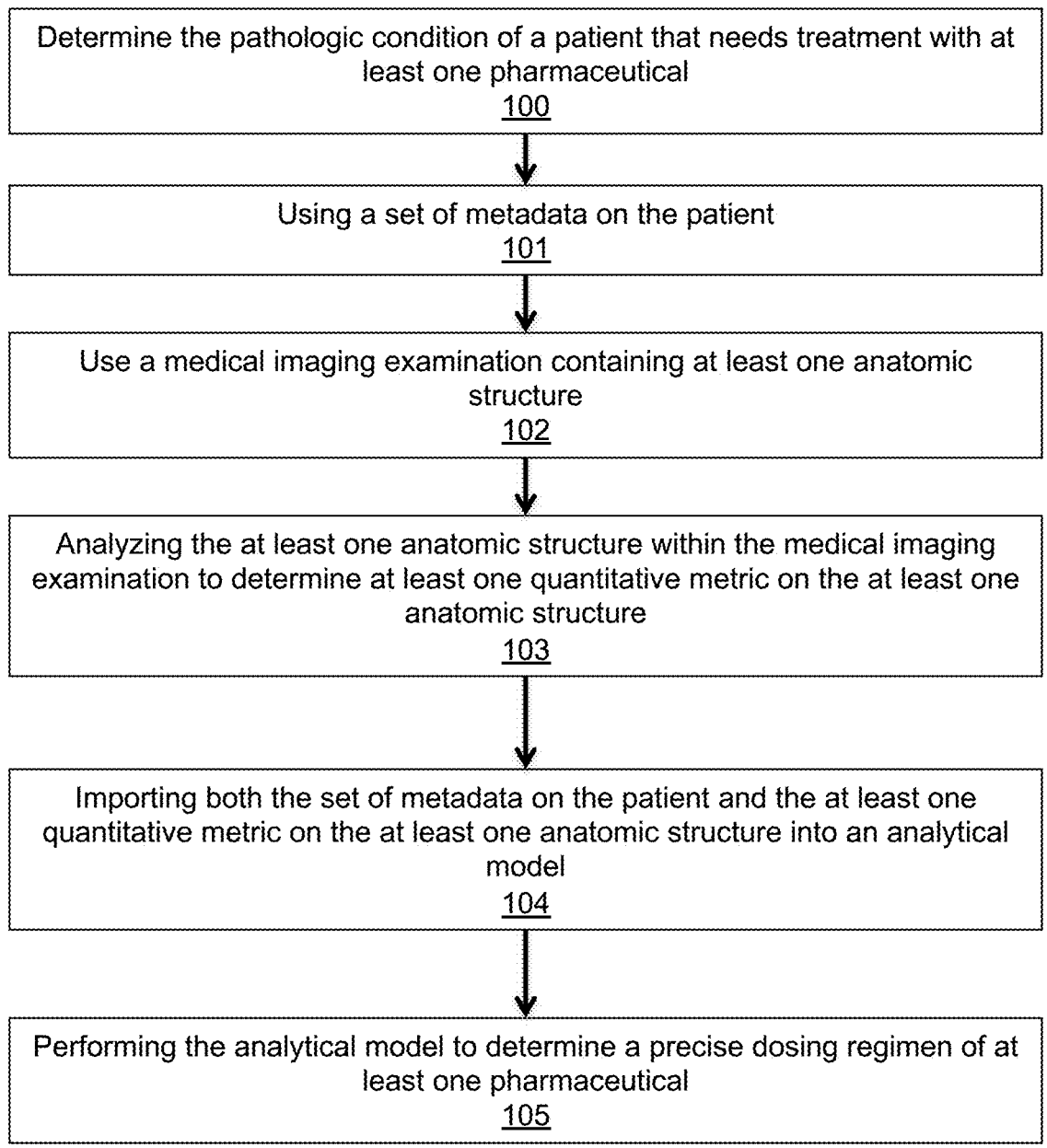
FIG. 1 illustrates a method of using quantitative and qualitative data from medical imaging examinations for precise dosing regimen.

FIG. 1 illustrates a method of using quantitative and qualitative data from medical imaging examinations for precise dosing regimen. 100 illustrates determining the pathologic condition of a patient that needs treatment with at least one radiopharmaceutical. For example, assume that the patient has a mild headache. The pharmaceutical to be used is Tylenol. 101 illustrates using metadata on the patient. For example, assume that the patient is a 75-year-old man and had liver function tests at the age of 74 years old, which revealed an AST of 45 and an ALT of 45. 102 illustrates using a medical imaging examination containing at least one anatomic structure. For example, assume that the 75-year-old man patient had a CT scan of the abdomen when he was 74 years old. 103 illustrates analyzing the at least one anatomic structure within the medical imaging examination to determine at least one quantitative metric on the at least one anatomic structure. For example, assume that the CT scan of the abdomen and pelvis included the liver, and the liver was segmented and a volume of 1940 mL. 104 is to import both the set of metadata on the patient and the at least one quantitative metric on the at least one anatomic structure into an analytical model. An example analytic model is described herein. A standard dose of Tylenol for a mild headache is 1000 mg. This analytic model takes a 10% penalty if the AST is elevated, a 10% penalty if the ALT is elevated and a 10% penalty if the liver volume is enlarged. 105 is to perform the analytical model to determine a precise dosing regimen of at least one pharmaceutical. This 75-year-old man would then have 20% dose adjustment (subtracting 20% or 200 mg) based on labs and a 10% dose adjustment (subtracting 10% or 100 mg) based on imaging biomarkers (liver volume).

Figure 2:
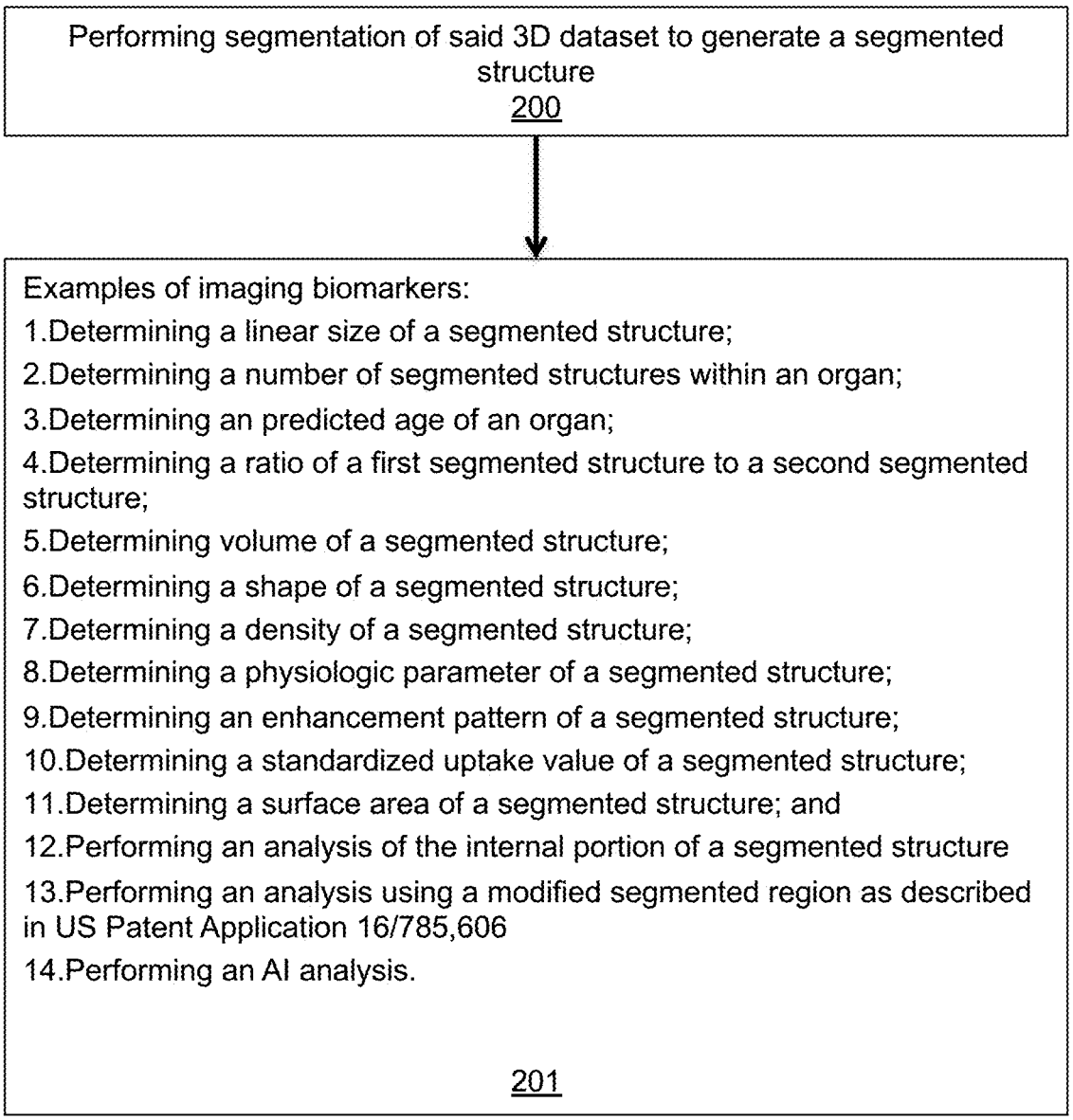
FIG. 2 illustrates determining quantitative pharmacologic dosing base imaging biomarkers.

FIG. 2 illustrates determining quantitative pharmacologic dosing base imaging biomarkers. A core concept of this inventive step is to convert a pre-image biomarker adjusted dose (pre-IBAD) to a post-image biomarker adjusted dose (post-IBAD). A pre-IBAD is an initial approximation of the dose such as would be determined through routine methods (looking up on epocrates). A post-MAD is a fine-tuned determination of the dose, which is adjusted based on an imaging biomarker. Several examples will be provided. 200 illustrates performing segmentation of said 3D dataset to generate a segmented structure. A variety of segmentation algorithms are available. For example, for neuroimaging applications, FreeSurfer can be utilized. A range of imaging biomarkers that can be used for precision dose adjustment. Some of which will be done through segmentation. 201 illustrates examples of imaging biomarkers and how they can be used to help determine dose. First, consider the example of a linear size of a segmented structure. This would be a simple analysis. For example, a longitudinal measurement of the kidney could be performed from the superior pole to the inferior pole. This single measurement could be used for dose adjustment. For example, suppose the average kidney was 12 cm and 1 gram of Vancomycin (pre-MAD) was going to be delivered. Assume that renal dosing based on kidney length (as the imaging biomarker) was to be performed and assume that a first patient had kidneys of 11.5 cm. A renal length corrected dose of 11.5/12×1000 mg could be performed, which would be equal to 958 grams (post-IBAD). Kidney length can be measured on a radiograph or an ultrasound. Thus, in some embodiments, a dose can be adjusted based on imaging biomarkers from a radiograph or an ultrasound. This precision dose could be manufactured (e.g., printed via a 3D printer).

Second, consider the example of a number of segmented structures within an organ. An example of this would be a number of segmented metastatic pulmonary nodules within the lungs. Assumed that a dose was determined through conventional means (pre-IBAD dose). Assume that for each metastatic lesion, the dose of chemotherapy was to be increased by 1.5% from the planned dose. Assume that a first person had 1 pulmonary nodule. This first person would receive 101.5% of the planned dose (post-IBAD dose for the first person). Assume that a second person had 11 pulmonary nodules. This second person would receive 116.5% of the planned dose (post-IBAD dose for the second person). Thus, the precision dose would be determined based on the number of segmented structures within an organ. This precision dose could be manufactured (e.g., printed via a 3D printer).

Third, consider the example of a predicted age of an organ. Assume that the predicted age of the liver for a first patient was 30 and that Tylenol was to be administered in a manner wherein the delivered dose is dependent upon the predicted age of an organ. For example, assume that the planned dose of Tylenol was 500 mg (pre-MAD). Assume that the adjustment was to give a standard dose for liver predicted age ranging from 0-60 and then for every age after 60, the dose would be decreased 2% for every year of predicted age. So, for a first patient with a liver predicted age of 50 who is scheduled to get 500 mg of Tylenol (pre-image biomarker adjusted dose), the first patient would receive 500 mg of Tylenol (post-IBAD). Note that in this instance, the pre-IBAD and post-IBAD are the same. For a second patient with a liver predicted age of 71 who is scheduled to get 500 mg (pre-image biomarker adjusted dose), the second patient would receive 500 mg×(100%−22%) or 390 mg of Tylenol (post-IBAD). Since the pharmacologic adjusted dose based on imaging biomarker would not be a standard dose that would be readily available (e.g., over the counter in a Tylenol bottle), the dose would have to be manufactured. Note that this precision dose (called precision dose because it is a pharmacologic adjusted dose based on an imaging biomarker) could be manufactured via a 3D printer.

Fourth, consider the example of determining a ratio of a first segmented structure to a second segmented structure and using this ratio to convert a pre-IBAD to a post-IBAD. In this example, a liver-kidney ratio is discussed. Assume that the normal liver volume to kidney volume (LKV) is 3 to 1 or 3.0. Assume that a pre-MAD of drug X is 1 gram. Assume that the model for determining the post-MAD dose is equal to pre-IBAD times patient LKV divided by normal LKV. Assume that a patient's LKV was 2.8. The post-IBAD of drug X would be 1.07 grams. This precision dose could be manufactured (e.g., printed via a 3D printer).

Fifth, consider the example of determine a post-IBAD based on the volume of a segmented structure. For example, assume that the post-IBAD dose is 10 mg of drug X for every 100 mL of organ. Assume that in this case the segmented structure is the kidneys and assume that the kidneys are 800 mL in volume. The post-IBAD would be equivalent to 800 mg times 10 mg of Drug X per 100 mL of organ. This would yield 80 mg of drug X as the post-MAD dose. This precision dose could be manufactured (e.g., printed via a 3D printer).

Sixth, consider the example of determining a post-IBAD based on a shape of a segmented structure. Assume that the shape of a mid-short axis view of a lumen of the left ventricle is oval at the end of ventricular diastole. Assume that a cardiac MRI was performed. Assume that the ratio of the semi-major axis to the semi-minor axis (SMATSMA) is used as a dose adjustment for drug X. Assume that the dose of Drug X is 1 gram divided by the SMATSMA. Assume that a first patient had a SMATSMA of 1.5. This first patient would receive a dose of 667 mg. Assume that a second patient had a SMATSMA of 1.1. This second patient would receive a dose of 909 mg. This precision dose could be manufactured (e.g., printed via a 3D printer). Thus, in some embodiments, a dose can be adjusted based on imaging biomarkers from an MM scan.

Seventh, consider the example of determining a post-IBAD based on a density of a segmented structure. For example, consider a density of segmented structure of the cancellous bone within the L1 vertebral body is 60 Hounsfield units. Assume that for every 1 Hounsfield unit below 60, the post-IBAD goes up by 1%. Assume that for Hounsfield Units of 60 or above, the pre-MAD will equal the post-IBAD. Assume that the pre-IBAD is 1000 mg of Calcium. Assume that a first patient has a recent CT scan of the abdomen and pelvis, and a segmentation process is implemented and that the Hounsfield units of the L1 vertebral body is 56 Hounsfield Units. This first patient would receive a post-IBAD of 1040 mg. This precision dose could be manufactured (e.g., printed via a 3D printer). A similar scenario could be performed for a DEXA scan with precision calcium dose adjustments based on T-scores or Z-scores. Thus, the dose of calcium delivered to an osteoporotic patient can be varied based on quantitative imaging biomarkers. Thus, in some embodiments, a dose can be adjusted based on imaging biomarkers from a CT scan. In other embodiments, a dose can be adjusted based on imaging biomarkers from a DEXA scan.

Eighth, consider the example of a physiologic parameter of a segmented structure. For example, assume that a nuclear medicine gastric emptying study was performed and the % emptying at 4 hours is normally greater than 90%. Assume that patients with delayed gastric emptying are given a pre-IBAD of 100 mg of Drug X. Assume that if a patient has 90% gastric emptying at 4 hours, they receive a dose of 50 mg of Drug X. Assume that for every percentage point below 90%, the dose increases by 2 mg. Therefore, a patient with a gastric emptying of 63% would receive a post-MAD of 104 mg. Thus, in some embodiments, a dose can be adjusted based on imaging biomarkers from a nuclear medicine scan. This precision dose could be manufactured (e.g., printed via a 3D printer).

Ninth, consider the example of using an enhancement pattern of a segmented structure to calculate a post-IBAD. Assume that a Drug X was going to be administered. Assume that there are 3 types of enhancement curves. Assume that the post-IBAD to be the same as pre-IBAD for a type 1 enhancement curve. Assume that the post-MAD is to be 10% increased as compared to the pre-MAD for a type 2 enhancement curve. Assume that the post-IBAD is to be 10% decreased as compared to the pre-IBAD for a type 3 enhancement curve. The post-IBAD adjustments for Drug X can be implemented and the precision dose manufactured (e.g., via 3D printer). Also, the volume of enhancement can also be used as an imaging biomarker.

Tenth, consider the example of a standardized uptake value of a segmented structure. Assume that a chemotherapy dose is adjusted based on the SUV wherein a sarcoma with a SUV of 15.0 is treated with Y mg of Drug X. Assume that the higher the SUV, the higher the dose of Drug Y. Assume a linear model. If a first person had a sarcoma with SUV of 15.0, the first person would be treated with Y mg of Drug X. If a second person had a sarcoma with SUV of 32.0, the second person would be treated with 2.13 times Y mg of Drug X. Thus, in some embodiments, a dose can be adjusted based on imaging biomarkers from a positron emission tomography (PET) scan.

Eleventh, consider the example of determining a surface area of a segmented structure. In order to determine the surface area, a cross-sectional imaging examination (e.g., CT or Mill scan) can be performed. Next, a segmentation algorithm can be performed to segment a structure. The surface of the segmented structure can subsequently be calculated. Assume that a dose is determined by the surface area of a segmented structure times 10 mg/cm$^2$. Assuming a surface area of 60 cm$^2$, the dose would be 600 mg. Thus, in some embodiments, the dose can be determined going straight from an imaging biomarker to a final dose without starting with a pre-MAD and doing dose adjustment. The precision dose can then be manufactured (e.g., via 3D printer).

Twelfth, consider performing an analysis of the internal portion of a segmented structure. For example, see U.S. patent application Ser. No. 16/785,606 IMPROVING IMAGE PROCESSING VIA A MODIFIED SEGMENTED STRUCTURE filed on Feb. 9, 2020. Please note that rather than adding conformal layers to the outside of a segmented structure, it would also be possible to eliminate layers in a conformal pattern in an inward direction. This could be performed so that the cortex of a vertebral body is subtracted and eliminated. This would allow the analysis of the inner portions of a structure. This represents a novel technique for analysis of the inner portions of a segmented structure. In some embodiments, a histogram can be performed of the voxels inside of this boundary. The analysis of the histogram can be utilized to determine the dose. For example, assuming the histogram analysis counts voxels above a certain threshold (Hounsfield units of 100 for bone density) within the region. Assume that a normal value is 100 1 mm-isotropic voxels per cm$^3$. Assume that less than daily calcium dose is needed to be calculated. Assuming that the dose of calcium is determined by this metric wherein for every 1 voxel below 100, 10 mg of calcium would be added. Assume a patient had a level of 85 1 mm-isotropic voxels per cm$^3$ with Hounsfield units of 100. This person would get 1150 mg of calcium daily. Thus, the pharmacologic dose is based on an imaging biomarker.

Thirteenth, consider performing an analysis using a modified segmented region as described in U.S. patent application Ser. No. 16/785,606. Assume that a patient has pyelonephritis. The amount of stranding surrounding the kidneys can be quantified (e.g., number of voxels per cm$^3$) that meet the threshold (between a pre-specified range, such as between +20 and +50). This quantitative value can be used as imaging biomarkers and utilized in ways as previously described to determine the dosing strategy.

Fourteenth, consider performing an analysis wherein big data is collected (imaging findings, pharmacologic dose, labs, rate of recovery, etc.). An artificial intelligence algorithm can perform analysis on an image and output the dose. A range of AI processes can be performed including explainable AI.

Finally, in some embodiments, radiologic dose adjustments (post-IBAD) can be combined with other methods of pharmacologic dose adjustments. These methods include but are not limited to the following: laboratory dose adjustment; weight-based dose adjustment; dermatologic finding-based dose adjustment (which can be performed via methods disclosed herein); and age-based dose adjustment.

Figure 3:
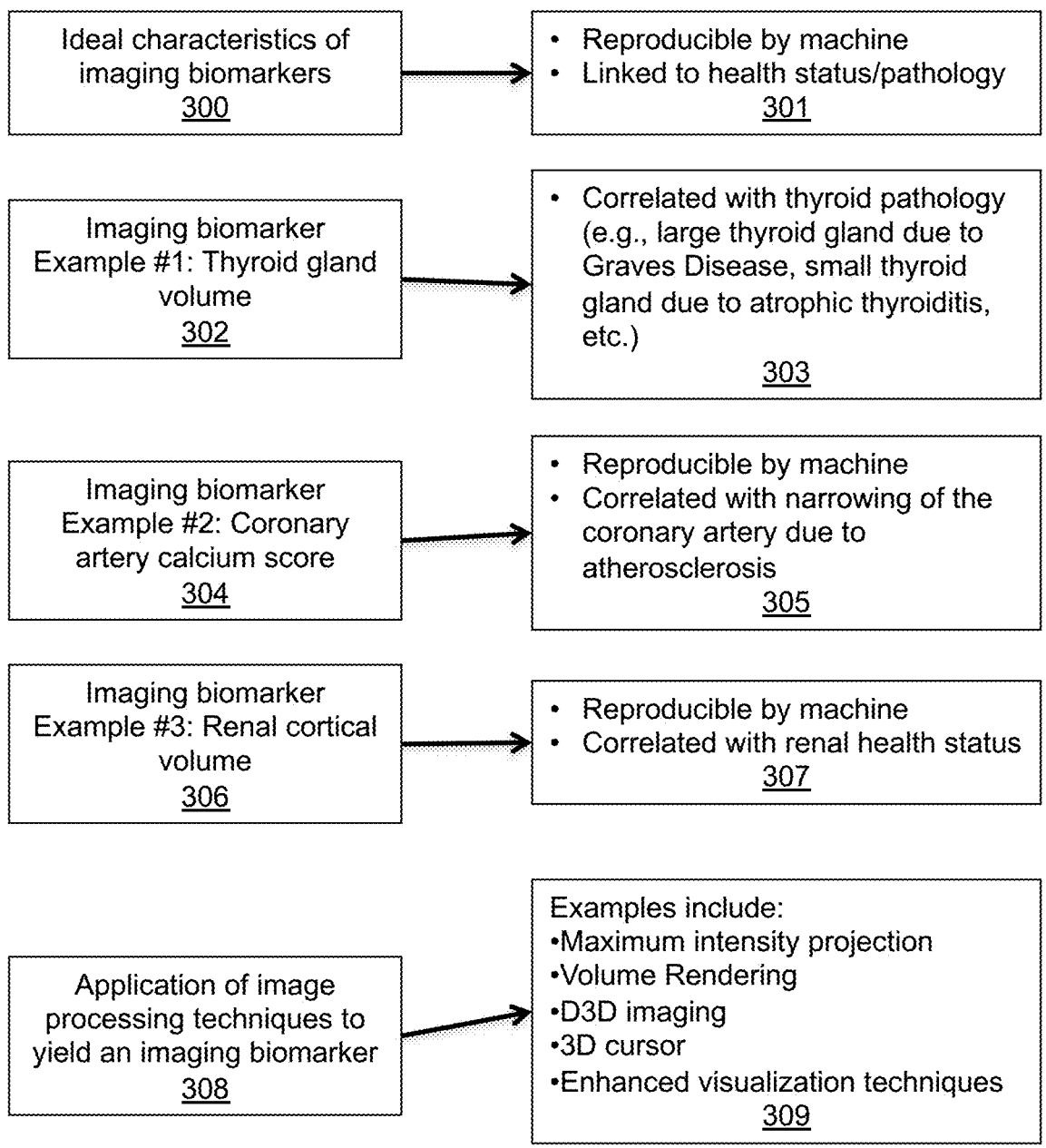
FIG. 3 illustrates examples of imaging biomarkers.

FIG. 3 illustrates examples of imaging biomarkers. 300 illustrates an important concept in this patent, which is the development of ideal characteristics of imaging biomarkers. 301 illustrates core concepts of the ideal imaging biomarkers, which include reproducibility and correlation with health status (e.g., the health of an organ) and pathology. 302 illustrates a first example of an imaging biomarker, which is thyroid gland volume. A thyroid gland volume can be obtained using volumetric imaging examinations including ultrasound, CT or MM scans. 303 illustrates correlating with thyroid pathology (e.g., large thyroid gland due to Graves Disease, small thyroid gland due to atrophic thyroiditis, etc.). 304 illustrates a second example of an imaging biomarker, which is coronary artery calcium score. A coronary artery calcium score can be obtained via a CT scan. 305 illustrates that the coronary artery calcium score is reproducible by a machine and is correlated with narrowing of the coronary artery due to atherosclerosis. 306 illustrates a third example of an imaging biomarker, which is renal cortical volume. 307 illustrates that the renal cortical volume is reproducible by a machine and is correlated with renal health status. 308 illustrates application of image processing techniques to yield an imaging biomarker. 109 illustrates examples, which include: performing segmentation of said 3D dataset to generate a segmented structure; determining volume of a segmented structure; performing a radiomic analysis of a segmented structure; performing maximum intensity projection; performing volume rendering; performing artificial intelligence analysis; performing D3D imaging; using 3D cursor; and other enhanced visualization techniques. A wide range of other techniques can be used for image processing to extract an imaging biomarker. In some embodiments, stereoscopic viewing of the virtual 3D mannequin is performed on an extended reality display unit, which is described in U.S. Pat. No. 8,384,771, METHOD AND APPARATUS FOR THREE DIMIENSIONAL VIEWING OF IMAGES, which is incorporated by reference in its entirety. This patent teaches image processing techniques including volume generation, filtering, rotation, and zooming.

In some embodiments, stereoscopic viewing of the virtual 3D mannequin is performed with convergence, which is described in U.S. Pat. No. 9,349,183, METHOD AND APPARATUS FOR THREE DIMIENSIONAL VIEWING OF IMAGES, which is incorporated by reference in its entirety. This patent teaches shifting of convergence. This feature can be used in combination with filtering.

In some embodiments, stereoscopic viewing can be performed using a display unit, which incorporates polarized lenses, which is described in U.S. Pat. No. 9,473,766, METHOD AND APPARATUS FOR THREE DIMIENSIONAL VIEWING OF IMAGES, which is incorporated by reference in its entirety.

In some embodiments, advancements to display units can be incorporated for viewing the virtual 3D mannequin, which are taught in U.S. patent application Ser. No. 16/828,352, SMART GLASSES SYSTEM and U.S. patent application Ser. No. 16/997,830, ADVANCED HEAD DISPLAY UNIT FOR FIRE FIGHTERS, which are both incorporated by reference in their entirety.

In some embodiments, advancements in display units are taught in U.S. patent application Ser. No. 17/120,109, ENHANCED VOLUME VIEWING, which is incorporated by reference in its entirety. Included herein is a head display unit, which is improved by incorporating geo-registration.

Some embodiments comprise utilizing an improved field of view on an extended reality head display unit, which is taught in U.S. patent application Ser. No. 16/893,291, A METHOD AND APPARATUS FOR A HEAD DISPLAY UNIT WITH A MOVABLE HIGH-RESOLUTION FIELD OF VIEW, which is incorporated by reference in its entirety.

In some embodiments, image processing steps can be performed using a 3D volume cursor, which is taught in U.S. Pat. No. 9,980,691, METHOD AND APPARATUS FOR THREE DIMIENSIONAL VIEWING OF IMAGES, and U.S. Pat. No. 10,795,457, INTERACTIVE 3D CURSOR, both of which are incorporated by reference in its entirety.

In some embodiments, a precision sub-volume can be utilized in conjunction with the virtual 3D mannequin, which is taught in U.S. patent application Ser. No. 16/927,886, A METHOD AND APPARATUS FOR GENERATING A PRECISION SUB-VOLUME WITHIN THREE-DIMENSIONAL IMAGE DATASETS, which is incorporated by reference in its entirety.

In some embodiments, viewing of a structure at two different time points can be performed using a ghost imaging technique, which is taught in U.S. Pat. No. 10,864,043, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, which is incorporated by reference in its entirety.

Some embodiments comprise selecting a specific surgical device for pre-operative planning, which is taught in U.S. patent application Ser. No. 17/093,322, A METHOD OF SELECTING A SPECIFIC SURGICAL DEVICE FOR PREOPERATIVE PLANNING, which is incorporated by reference in its entirety.

Some embodiments comprise, generating the virtual 3D mannequin using techniques described in U.S. patent application Ser. No. 16/867,102, METHOD AND APPARATUS OF CREATING A COMPUTER-GENERATED PATIENT SPECIFIC IMAGE, which is incorporated by reference in its entirety. Key techniques include using patient factors (e.g., history, physical examination findings, etc.) to generate a volume.

Some embodiments comprise advanced image processing techniques available to the user of the virtual 3D mannequin, which are taught in U.S. Pat. No. 10,586,400, PROCESSING 3D MEDICAL IMAGES TO ENHANCE VISUALIZATION, and U.S. Pat. No. 10,657,731, PROCESSING 3D MEDICAL IMAGES TO ENHANCE VISUALIZATION, both of which are incorporated by reference in its entirety.

Some embodiments comprise performing voxel manipulation techniques so that portions of the virtual 3D mannequin can be deformed and move in relation to other portions of the virtual 3D mannequin, which is taught in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

Some embodiments comprise generating at least some portions of the virtual 3D mannequin through artificial intelligence methods and performing voxel manipulation thereof, which is taught in U.S. patent application Ser. No. 16/736,731, RADIOLOGIST-ASSISTED MACHINE LEARNING WITH INTERACTIVE, VOLUME SUBTENDING 3D CURSOR, which is incorporated by reference in its entirety.

Some embodiments comprise wherein at least some component of the inserted 3D dataset into the virtual 3D mannequin are derived from cross-sectional imaging data fine-tuned with phantoms, which is taught in U.S. patent application Ser. No. 16/752,691, IMPROVING IMAGE QUALITY BY INCORPORATING DATA UNIT ASSURANCE MARKERS, which is incorporated by reference in its entirety.

Some embodiments comprise utilizing halo-type segmentation techniques, which are taught in U.S. patent application Ser. No. 16/785,606, IMPROVING IMAGE PROCESSING VIA A MODIFIED SEGMENTED STRUCTURE, which is incorporated by reference in its entirety.

Some embodiments comprise using techniques for advanced analysis of the virtual 3D mannequin taught in U.S. patent application Ser. No. 16/939,192, RADIOLOGIST ASSISTED MACHINE LEARNING, which are incorporated by reference in its entirety.

Some embodiments comprise performing smart localization from a first virtual 3D mannequin to a second virtual 3D mannequin, such as in an anatomy lab, which is performed via techniques taught in U.S. patent application Ser. No. 17/100,902, METHOD AND APPARATUS FOR AN IMPROVED LOCALIZER FOR 3D IMAGING, which is incorporated by reference in its entirety.

Some embodiments comprise performing a first imaging examination with a first level of mechanical compression and a second imaging examination with a second level of mechanical compression and analyzing differences therein, which is taught in U.S. patent application Ser. No. 16/594,139, METHOD AND APPARATUS FOR PERFORMING 3D IMAGING EXAMINATIONS OF A STRUCTURE UNDER DIFFERING CONFIGURATIONS AND ANALYZING MORPHOLOGIC CHANGES, which is incorporated by reference in its entirety.

Some embodiments comprise displaying the virtual 3D mannequin in an optimized image refresh rate, which is taught in U.S. patent application Ser. No. 16/842,631, A SMART SCROLLING SYSTEM, which is incorporated by reference in its entirety.

Some embodiments comprise displaying the virtual 3D mannequin using priority volume rendering, which is taught in U.S. Pat. No. 10,776,989, A METHOD AND APPARATUS FOR PRIORITIZED VOLUME RENDERING, which is incorporated by reference in its entirety.

Some embodiments comprise displaying the virtual 3D mannequin using tandem volume rendering, which is taught in U.S. patent Ser. No. 17/033,892, A METHOD AND APPARATUS FOR TANDEM VOLUME RENDERING, which is incorporated by reference in its entirety.

Some embodiments comprise displaying images in an optimized fashion by incorporating eye tracking, which is taught in U.S. patent application Ser. No. 16/936,293, IMPROVING VISUALIZATION OF IMAGES VIA AN ENHANCED EYE TRACKING SYSTEM, which is incorporated by reference in its entirety.

Some embodiments comprise enhancing collaboration for analysis of the virtual 3D mannequin by incorporating teachings from U.S. patent application Ser. No. 17/072,350, OPTIMIZED IMAGING CONSULTING PROCESS FOR RARE IMAGING FINDINGS, which is incorporated by reference in its entirety.

Some embodiments comprise improving multi-user viewing of the virtual 3D mannequin by incorporating teachings from U.S. patent application Ser. No. 17/079,479, AN IMPROVED MULTI-USER EXTENDED REALITY VIEWING TECHNIQUE, which is incorporated by reference in its entirety.

Some embodiments comprise improving analysis of images through use of geo-registered tools, which is taught in U.S. Pat. No. 10,712,837, USING GEO-REGISTERED TOOLS TO MANIPULATE THREE-DIMENSIONAL MEDICAL IMAGES, which is incorporated by reference in its entirety.

Some embodiments comprise integration of virtual tools with geo-registered tools, which is taught in U.S. patent application Ser. No. 16/893,291, A METHOD AND APPARATUS FOR THE INTERACTION OF VIRTUAL TOOLS AND GEO-REGISTERED TOOLS, which is incorporated by reference in its entirety.

In some embodiments blood flow is illustrated in the virtual 3D mannequin, which is taught in U.S. patent application Ser. No. 16/506,073, A METHOD FOR ILLUSTRATING DIRECTION OF BLOOD FLOW VIA POINTERS, which is incorporated by reference in its entirety and U.S. Pat. No. 10,846,911, 3D IMAGING OF VIRTUAL FLUIDS AND VIRTUAL SOUNDS, which is also incorporated by reference in its entirety.

Some embodiments also involve incorporation of 3D printed objects to be used in conjunction with the virtual 3D mannequin. Techniques herein are disclosed in U.S. patent Ser. No. 17/075,799, OPTIMIZING ANALYSIS OF A 3D PRINTED OBJECT THROUGH INTEGRATION OF GEO-REGISTERED VIRTUAL OBJECTS, which is incorporated by reference in its entirety.

Some embodiments also involve a 3D virtual hand, which can be geo-registered to the virtual 3D mannequin. Techniques herein are disclosed in U.S. patent application Ser. No. 17/113,062, A METHOD AND APPARATUS FOR A GEO-REGISTERED 3D VIRTUAL HAND, which is incorporated by reference in its entirety.

Some embodiments comprise utilizing images obtained from U.S. patent application Ser. No. 16/654,047, METHOD TO MODIFY IMAGING PROTOCOLS IN REAL TIME THROUGH IMPLEMENTATION OF ARTIFICIAL, which is incorporated by reference in its entirety.

Some embodiments comprise utilizing images obtained from U.S. patent application Ser. No. 16/597,910, METHOD OF CREATING AN ARTIFICIAL INTELLIGENCE GENERATED DIFFERENTIAL DIAGNOSIS AND MANAGEMENT RECOMMENDATION TOOL BOXES DURING MEDICAL PERSONNEL ANALYSIS AND REPORTING, which is incorporated by reference in its entirety.

Figure 4:
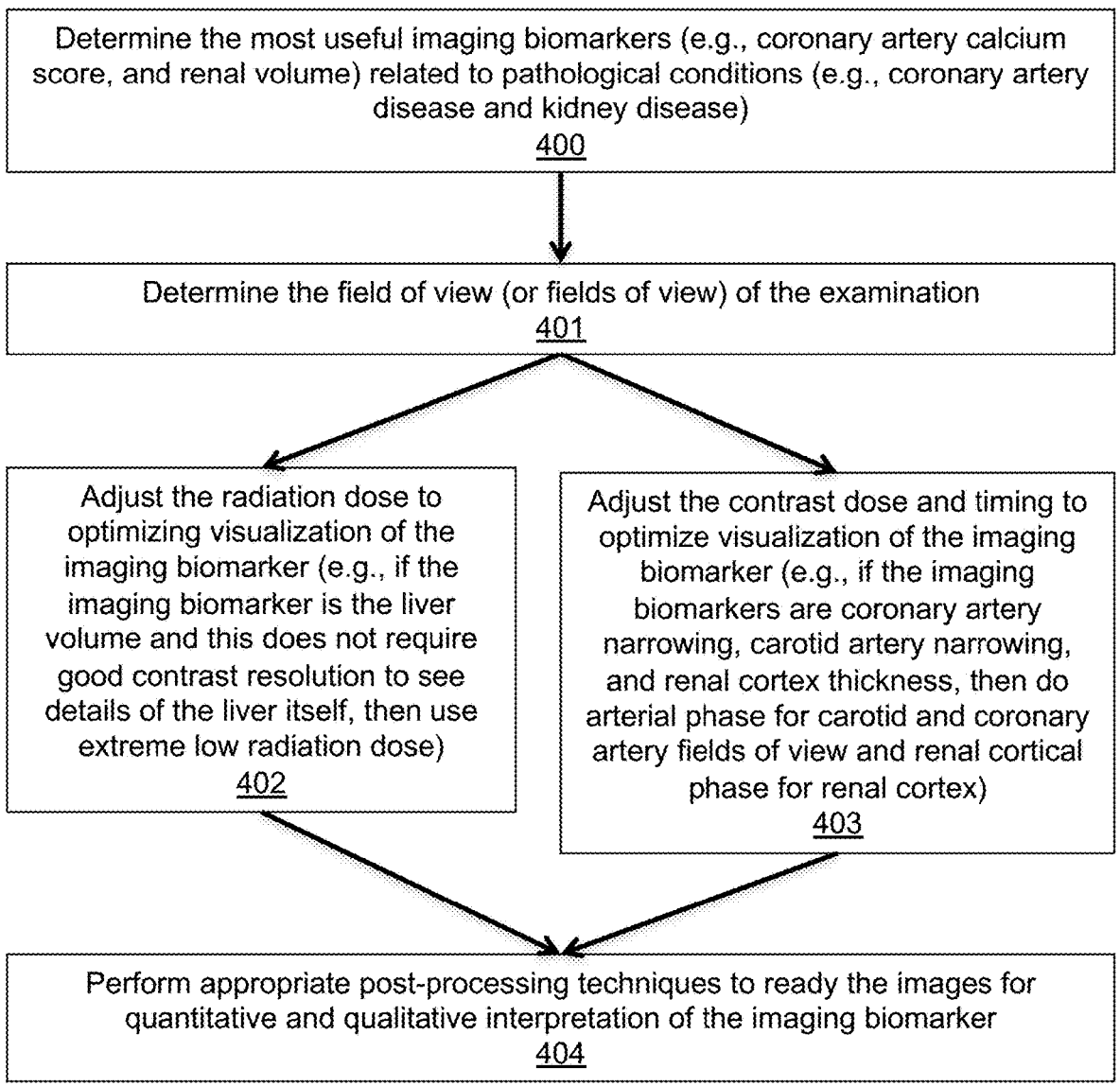
FIG. 4 illustrates designing imaging protocols used to optimize visualization of imaging biomarkers for pharmacologic dosing strategy.

FIG. 4 illustrates designing imaging protocols used to optimize visualization of imaging biomarkers for pharmacologic dosing strategy. 400 illustrates determining the most useful imaging biomarkers (e.g., coronary artery calcium score and renal volume) related to pathological conditions (e.g., coronary artery disease and kidney disease). 401 illustrates determining the field of view (or fields of view) of the examination. Note that in some cases the imaging examination is already acquired and a previously acquired imaging examination may have already been performed with the appropriate imaging biomarker. 402 illustrates adjusting the radiation dose to optimizing visualization of the imaging biomarker (e.g., if the imaging biomarker is the liver volume and this does not require good contrast resolution to see details of the liver itself, then use extreme low radiation dose). Alternatively, if the imaging biomarker requires good contrast resolution (e.g., characterizing a liver's intrinsic properties or gray-white differentiation of the brain on a head CT), then it would be desired to have a higher radiation dose. 403 illustrates adjusting the contrast dose and timing to optimize visualization of the imaging biomarker (e.g., if the imaging biomarkers are coronary artery narrowing, carotid artery narrowing, and renal cortex thickness, then do arterial phase for carotid and coronary artery fields of view and renal cortical phase for renal cortex). 404 illustrates performing the appropriate post-processing techniques to ready the images for quantitative and qualitative interpretation of the imaging biomarker.

FIG. 5 illustrates a slice-by-slice based CT radiation dosing strategy. 500 illustrates determining the slice location of the imaging biomarkers of interest (e.g., via scout image, via external landmarks, via very low dose CT images). 501 illustrates determining the minimum quality of the image (e.g., spatial resolution, contrast resolution, noise, etc.) for each imaging biomarkers of interest (e.g., if the imaging biomarker is the volume of the kidney than design the protocol so that each slice has a very low radiation dose scan to derive accurate estimate of the volume of the kidney, if the imaging biomarker is an accurate Hounsfield density measurement of the parenchyma of the kidney then need a medium dose of one single CT slice for this imaging biomarker). In doing so, this represents a novel type of imaging examination. Conventional CT examinations have attempted to provide excellent image quality on all slices. This technique teaches that some slices are optimized (e.g., optimized kVp and mA) for superb contrast resolution and other slices are deliberately acquired with sub-optimal (e.g., a lower kVp and mA) contrast resolution. However, this technique is useful because it selectively acquires images for at various qualities to reduce overall dose. Similarly, GANs can be performed for the noisy, low-dose slices to improve the image quality if desired. This is further taught in U.S. patent application Ser. No. 16/703,629, RADIOLOGIST-ASSISTED MACHINE LEARNING WITH INTERACTIVE, VOLUME SUBTENDING 3D CURSOR, which is incorporated by reference in its entirety. Note that some slices are of very low dose and other slices are of medium dose. This helps achieve accurate Hounsfield measurements for analysis (e.g., radiomics). 502 illustrates performing the CT scan with specific acquisition parameters derived above (e.g., mAs, kVp, etc.) for each slice in the scan (e.g., do ultra-low dose CT scan of the kidney to generate precise volume as a first biomarker and do regular dose image of a single slice through the mid-kidney to understand the average Hounsfield units). This combination can yield a dataset optimized for assessment of imaging biomarkers.

Figure 6:
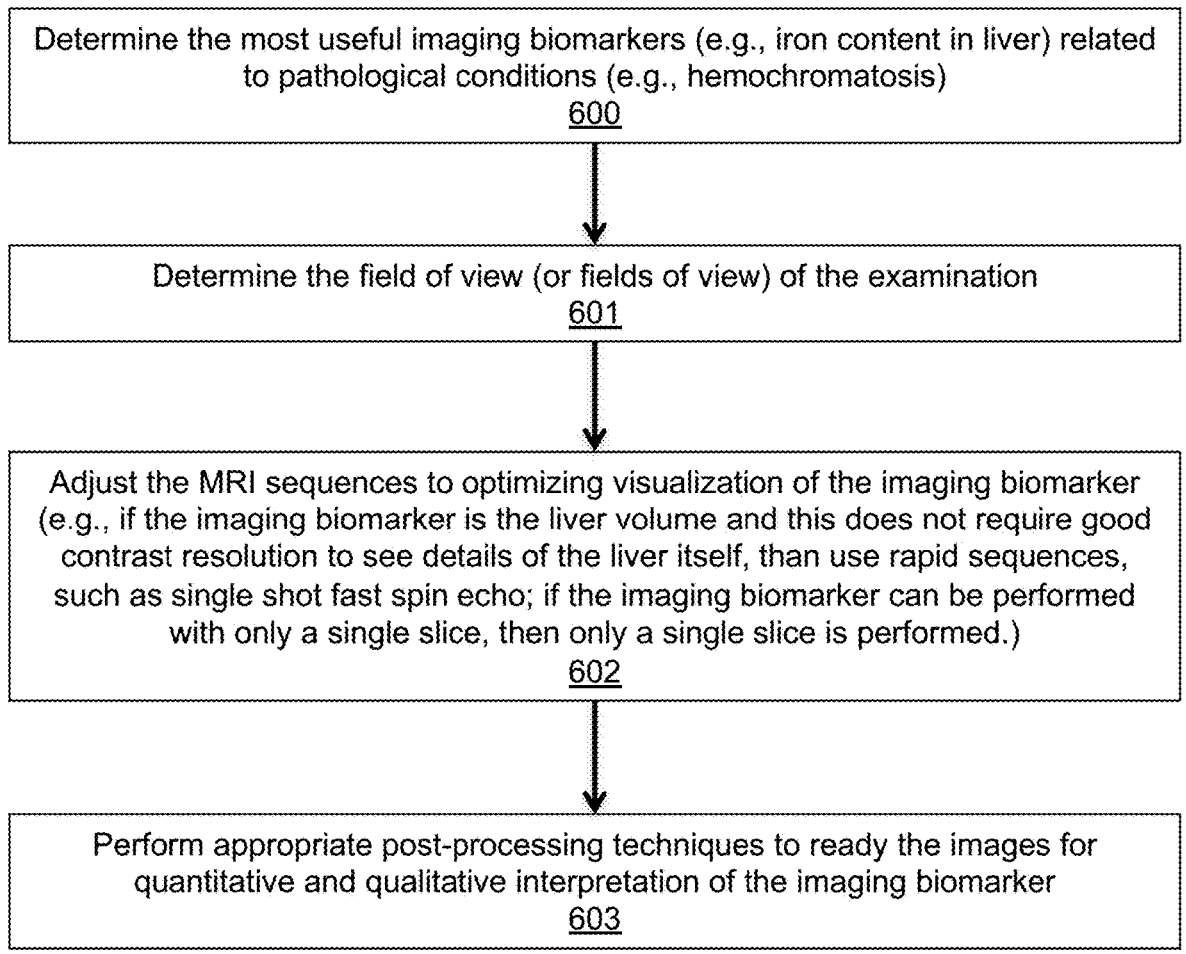
FIG. 6 illustrates designing an MRI protocols used for pharmacologic dosing strategy.

FIG. 6 illustrates designing an MRI protocols used for pharmacologic dosing strategy. 600 illustrates determining the most useful imaging biomarkers (e.g., coronary artery disease and renal health) related to pathological conditions (e.g., coronary artery disease kidney disease). 601 illustrates determining the field of view (or fields of view) of the examination. 602 illustrates adjusting the MRI sequences to optimizing visualization of the imaging biomarker. For example, if the imaging biomarker is the liver volume and this does not require good contrast resolution to see details of the liver itself, then use rapid sequences, such as single shot fast spin echo. For example, if the imaging biomarker can be performed with only a single slice, then only a single slice is performed. 603 illustrates performing appropriate post-processing techniques to ready the images for quantitative and qualitative interpretation of the imaging biomarker.

FIG. 7 illustrates a slice-by-slice based MR acquisition strategy. 700 illustrates determining the slice location of the imaging biomarkers of interest (e.g., via scout image, via external landmarks, via MR images). 701 illustrates determining the minimum quality of the image (e.g., spatial resolution, contrast resolution, noise, etc.) for each imaging biomarkers of interest. For example, if the imaging biomarker is the volume of the kidney, then design the protocol so that each slice has a very rapid acquisition to derive accurate estimate of the volume of the kidney. If the imaging biomarker is an accurate measurement of the parenchyma of the kidney, then need a different, more time-consuming acquisition slice for this imaging biomarker. This technique teaches that some slices are optimized (e.g., time to repetition, TR and time to echo, TE, flip angle, etc.) for superb contrast resolution and other slices are deliberately acquired with sub-optimal (e.g., different TR, TE, flip angle, etc.) contrast resolution. However, this technique is useful because it selectively acquires images for at various qualities to reduce acquisition time and specific absorption rate (SAR). 702 illustrates performing the MRI scan with specific acquisition parameters derived above for each slice in the scan. For example, do rapid acquisition of the kidney to generate precise volume as a first biomarker and do long acquisition image of a single slice through the mid-kidney for improved contrast resolution and characterization thereof.

Figure 8:
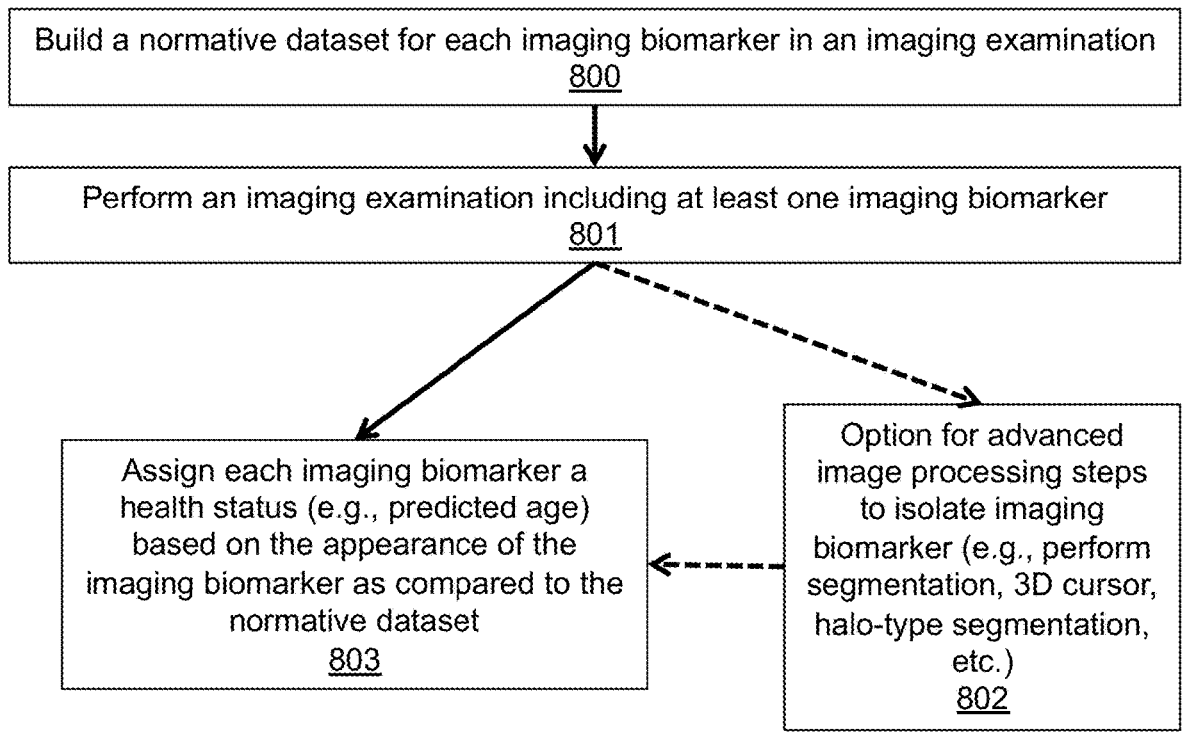
FIG. 8 illustrates labeling imaging biomarkers with a health score (e.g., predicted age) for precision pharmacologic therapy.

FIG. 8 illustrates labeling imaging biomarkers with a health score (e.g., predicted age) for precision pharmacologic therapy. 800 illustrates building a normative dataset for each imaging biomarker in an imaging examination. For example, a database may include MM scans of the abdomen and pelvis of healthy men of varying ages. 801 illustrates performing an imaging examination including at least one imaging biomarker. For example, an MRI scan can be performed on a 65-year-old man, who is the subject of interest. 802 illustrates an option for advanced image processing steps to isolate imaging biomarker (e.g., perform segmentation, 3D cursor, halo-type segmentation, etc.). For example, the kidney of the 65-year-old man subject of interest can be analyzed. 803 illustrates assign each imaging biomarker a health status (e.g., predicted age) based on the appearance of the imaging biomarker as compared to the normative dataset. For example, an artificial intelligence algorithm can be applied to predict the age of a kidney of the subject of interest. Assume, that the AI algorithm predicts that the kidneys most closely match that of a 50-year man.

This process can be performed for multiple structures within the imaging dataset, such as the liver, spleen, pancreas, adrenal glands, kidneys, bowel, mesentery, bladder, prostate, and bones. Then, a predicted age (which is a marker of health status) can be determined for each organ. A formula can be applied to determine the age of a patient. For example, assume that the liver, spleen, pancreas, adrenal glands, kidneys, bowel, mesentery, bladder, prostate, and bones were each worth 10%. Assume that the liver had an age of 51. Assume that the spleen had an age of 60. Assume that the pancreas had an age of 70. Assume that the adrenal glands had an age of 60. Assume that the kidneys had an age of 50. Assume that the bowel had an age of 60. Assume that the mesentery had an age of 65. Assume that the bladder had an age of 70. Assume that the prostate had an age of 50. Assume that the bones had an age of 60. The average predicted age would be 596/10 or 59.6 years. The patient's kidneys would be doing well with an average age of 50 and the patient's pancreas and bladder would be doing more poorly. This analysis can be used for selection of a pharmaceutical. For example, if a physician had two choices. A first choice is a pharmaceutical that negatively affects the pancreas. And a second choice is a pharmaceutical that negatively affects the kidneys. It would be prudent to select the pharmaceutical that negatively affects the kidneys because of the relatively good performance relative to other organs. As a minimum, it would be prudent to inform the physician of this so the physician can consider this in the care he/she provides.

Figure 9:
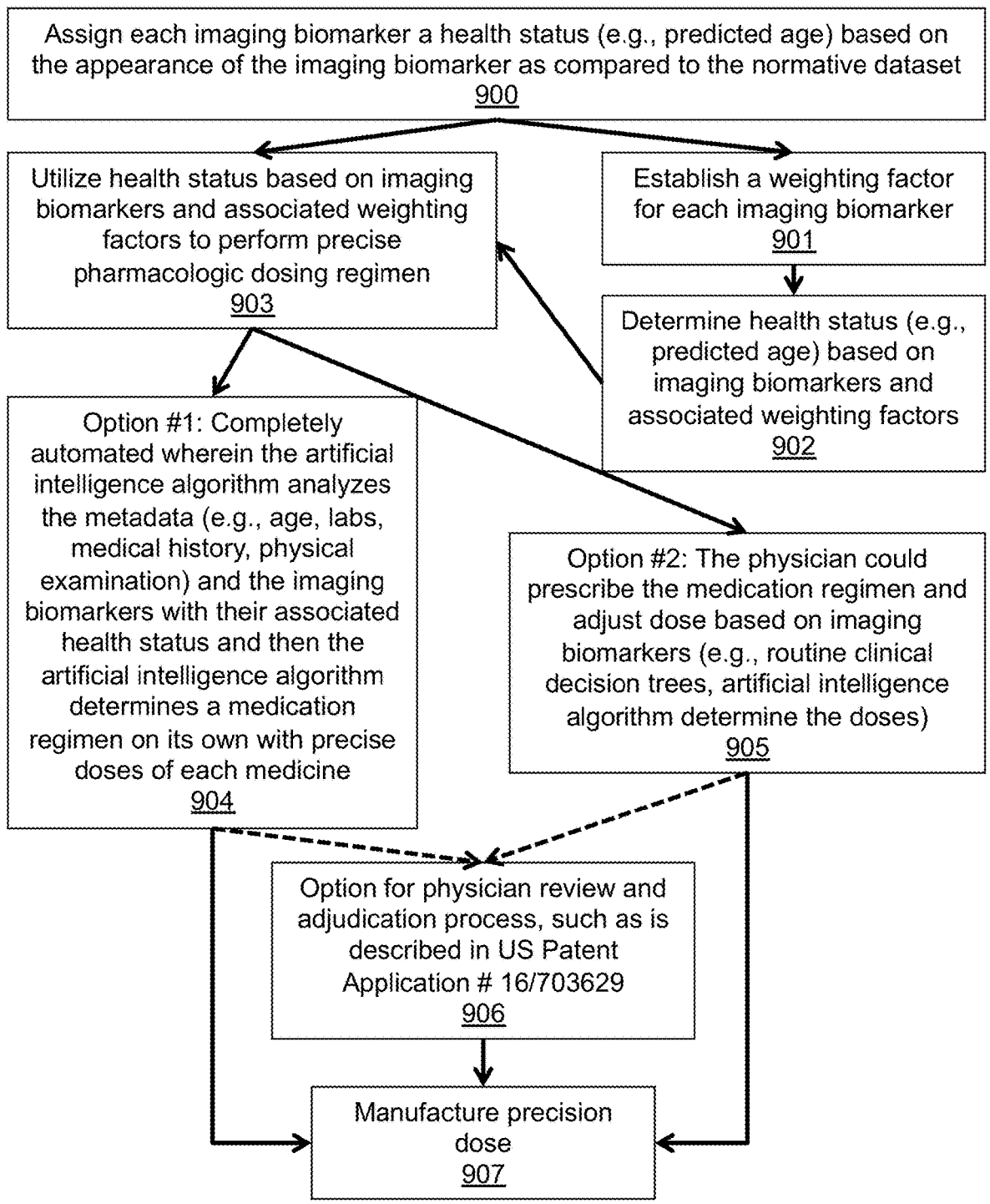
FIG. 9 illustrates utilizing weighting factors associated with imaging biomarkers for precision therapy.

FIG. 9 illustrates utilizing weighting factors associated with imaging biomarkers for precision therapy. 900 illustrates assigning each imaging biomarker a health status (e.g., predicted age) based on the appearance of the imaging biomarker as compared to the normative dataset. 901 illustrates establish a weighting factor for each imaging biomarker. 902 illustrates determine health status (e.g., predicted age) based on imaging biomarkers and associated weighting factors. For example, in some embodiments, ten segmented structures (e.g., liver, spleen, pancreas, adrenal glands, kidneys, bowel, mesentery, bladder, prostate, and bones) are used for an abdomen/pelvis CT scan and each segmented structure has equal weight. In other embodiments, the organs are allocated different weights, such as: liver weight of 20%; spleen weight of 5%; pancreas weight of 7%; adrenal glands of 5%; kidneys of 25%; bowel weight of 5%; mesentery weight of 5%; bladder weight of 5%; prostate weight of 3%; and bones weight of 20%. 903 illustrates utilize health status based on imaging biomarkers and associated weighting factors to perform precise pharmacologic dosing regimen. A predicted age for each organ can be performed. A weighting factor can be performed. Then, these can be used together to determine the overall health status and predicted age for the abdomen/pelvis CT scan. 904 illustrates a first option comprising a completely automated process wherein the artificial intelligence algorithm analyzes the metadata (e.g., age, labs, medical history, physical examination, diagnoses including the most recent diagnosis, such as pneumonia) and the imaging biomarkers with their associated health status and then the artificial intelligence algorithm determines a medication regimen (e.g., penicillin) on its own with precise doses of each medicine. 905 illustrates a second option comprising wherein the physician could prescribe the medication regimen and adjust dose based on imaging biomarkers (e.g., routine clinical decision trees, artificial intelligence algorithm determine the doses). Note that in both option #1 and option #2, the preferred embodiment is for the dose to be adjusted based on imaging biomarkers. 906 is an option for the physician review and adjudication process, such as is described in U.S. patent application Ser. No. 16/703,629. 907 illustrates manufacturing a precision dose.

Figure 10:
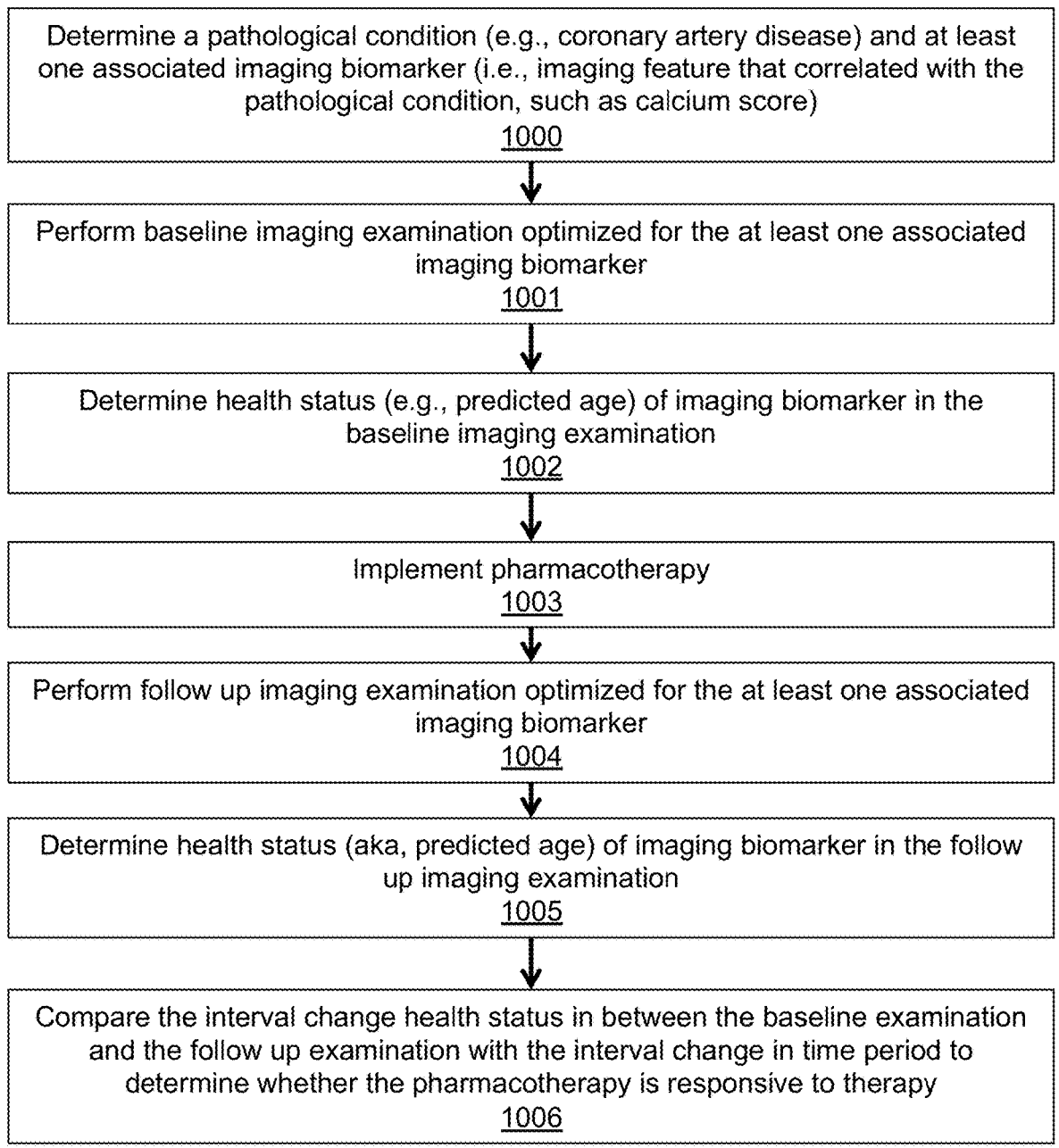
FIG. 10 illustrates a quantitative method to determine whether an imaging biomarker is responsive to pharmacotherapy.

FIG. 10 illustrates a quantitative method to determine whether an imaging biomarker is responsive to pharmacotherapy. 1000 illustrates determining a pathological condition (e.g., coronary artery disease) and at least one associated imaging biomarker (i.e., imaging feature that correlated with the pathological condition, such as calcium score). 1001 illustrates performing baseline imaging examination optimized for the at least one associated imaging biomarker. For example, a calcium score of 212. 1002 illustrates determining health status (e.g., predicted age) of imaging biomarker in the baseline imaging examination. A calcium score of 212 corresponds to a predicted age of 78. 1003 illustrates implement pharmacotherapy. For example, prescribing a statin. 1004 illustrates performing follow up imaging examination optimized for the at least one associated imaging biomarker. 1005 illustrates determining health status (aka, predicted age) of imaging biomarker in the follow up imaging examination. For example, on the follow up examination five years later, the calcium score is 213, which still corresponds to a predicted age of 78. 1006 illustrates comparing the interval change health status in between the baseline examination and the follow up examination with the interval change in time period to determine whether the pharmacotherapy is responsive to therapy. A rate of progression of the imaging biomarker can be determined. For example, if there is no progression of the imaging biomarker of coronary artery calcium score over a five-year period, then the conclusion is that the pharmacotherapy is appropriately treating the condition. If there is progression at a too high of a rate (e.g., imaging biomarker predicts a 10-year advancement in age, but only 5 years have passed), then, the pharmacologic treatment plan can be adjusted accordingly. This would be consistent with a slow progression of this imaging biomarker.

FIG. 11 illustrates qualitative method to test whether an imaging biomarker is responsive to pharmacotherapy. 1100 illustrates determining a pathological condition (e.g., idiopathic pulmonary fibrosis) and at least one associated imaging biomarker (i.e., imaging feature that correlated with the pathological condition, such as honeycombing). 1101 illustrates performing a baseline imaging examination optimized for the at least one associated imaging biomarker. 1102 illustrates determining health status (aka, subjective severity scoring system) of imaging biomarker in the baseline imaging examination. 1103 illustrates implement pharmacotherapy. 1104 illustrates performing follow up imaging examination optimized for the at least one associated imaging biomarker. 1105 illustrates determining health status (e.g., subjective severity scoring system) of imaging biomarker in the follow up imaging examination. This can be performed by using artificial intelligence algorithm. 1106 illustrates comparing the interval change health status in between the baseline examination and the follow up examination (e.g., mild progression) with the interval change in time period (e.g., 5 years) to determine whether the pharmacotherapy is responsive to therapy (e.g., slower than normal progression, normal progression, faster than normal progression).

FIG. 12 illustrates longitudinal analysis of imaging biomarkers for precision monitoring of pharmacotherapy effectiveness. A table is shown. In the calendar year row, 2022, 2023, 2024, 2025, 2026 and 2027 are shown. The chronological age of the patient at these years is 51, 52, 53, 54, 55, and 56. The imaging biomarker of the health status of the kidney is 51, 52, 53, 54, 55, and 56 during these years. The imaging biomarker of the health status of the pancreas is 51, 52, 53, 54, 55, and 56. The imaging biomarker of the health status of the coronary artery calcifications is 60, 60, 60, 60, 60, and 61 during these years. Note that this useful since at the beginning of pharmacotherapy at age 51 in 2022, the coronary artery calcium score was 9 years advanced over chronological age, but at chronological age of 56 in 2027, the coronary artery calcium score was only 5 years advanced over chronological age. This would represent treatment success because it identified the weakest link of the patient and addressed it by implementing pharmacotherapy. Finally, the imaging biomarker of honeycombing for pulmonary fibrosis is classified as mild at all years therefore no progression is noted.

FIG. 13 illustrates delivering system of the health status of imaging biomarkers to the health care professional or patient. In this chart, the patient chronological age of 50.1 is shown. The imaging biomarker ages are also shown with heart at 48.5, lungs at 49.0, liver at 45.1, pancreas at 46.8, adrenal glands at 49.0, and kidneys at 49.5.

FIG. 14 illustrates image-guided medication prioritization strategy. 1400 illustrates performing an imaging examination wherein the field of view includes at least one imaging biomarker. For example, optimize imaging examination for imaging biomarker. This can be discussed using image processing techniques discussed in the patents and patent applications, which are incorporated by reference in their entirety. Additionally, perform routine radiologic interpretation of the examination for incidental pathologies, which is performed by a radiologist. Also, perform quantitative interpretation of imaging biomarker and qualitative interpretation of imaging biomarker. 1401 illustrates determining the expected rate of progression of at least one imaging biomarker. To accomplish this, use actual patient data compare interval change of imaging biomarker over multiple examinations. Additionally, use repository of population data to obtain expected rate of progression. 1402 illustrates plotting the expected rate of progression of each imaging biomarker over time. This can be performed using computer simulations including AI processes. 1403 illustrates determining the condition that is linked to at least one imaging biomarker that is most threatening to the patient. For example, it is important to determine the condition that is predicted to cause negative effects. For example, which condition is most likely to cause disability the earliest? Which condition is most likely to cause death the earliest? 1404 illustrates analyzing metadata for other factors related to pharmacologic regimen (e.g., labs, physical examination, medication compliance, etc.). 1405 illustrates designing a pharmacologic regimen to prioritize conditions that are most threatening to the patient. For example, if a patient has an aneurysm, a key goal of pharmacotherapy is to optimize blood pressure control to halt progression.

Figure 15:
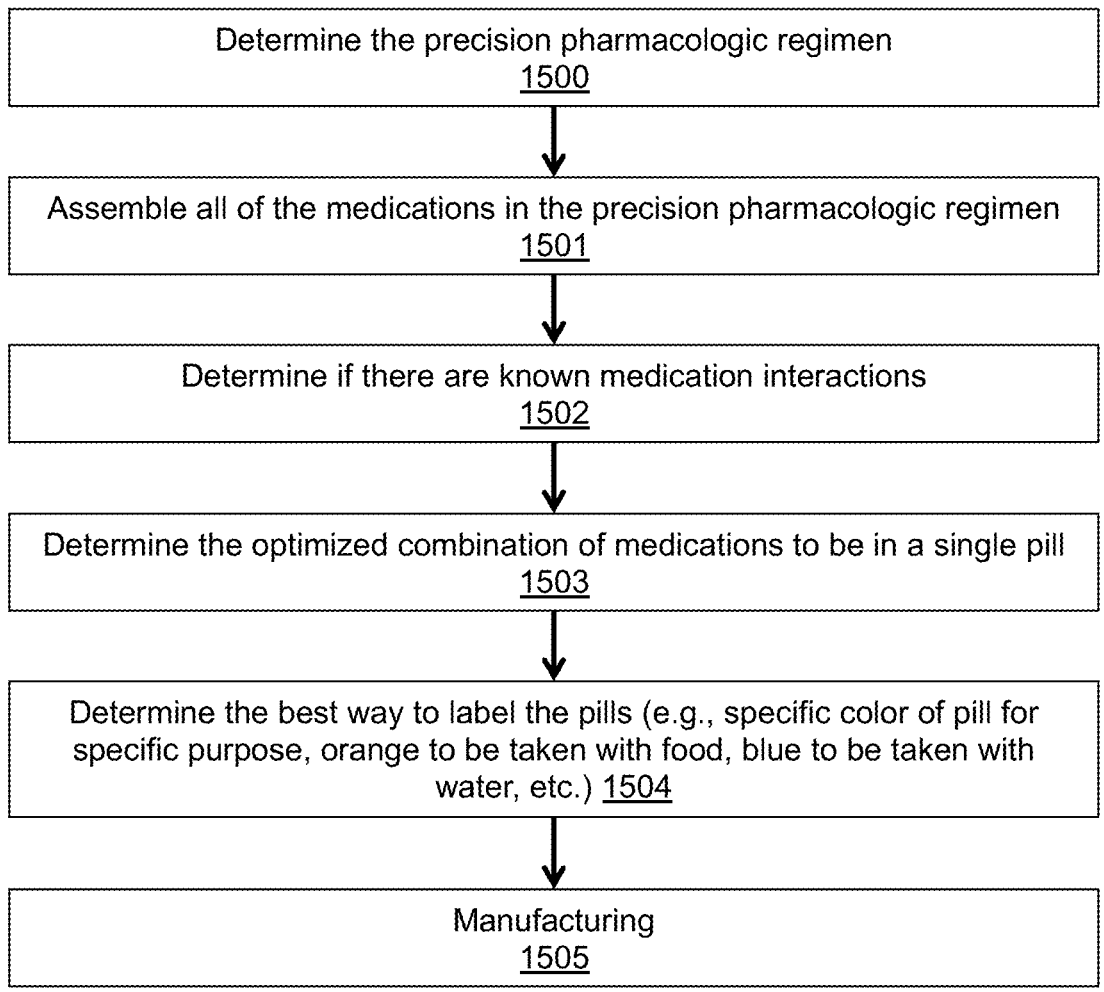
FIG. 15 illustrates manufacturing precision pharmacology dose.

FIG. 15 illustrates manufacturing precision pharmacology dose. 1500 illustrates determining the precision pharmacologic regimen. 1501 illustrates assembling all of the medications in the precision pharmacologic regimen. 1502 illustrates determining if there are known medication interactions. For example, some medications should not be combined in the same pill (e.g., fish oil and gingko biloba). 1503 illustrates determining the optimized combination of medications to be in a single pill. For example, those medications that are best to be taken on an empty stomach are combined into a first pill. Those medications that are best to be taken with water are combined to a second pill. Those medications that are best to be taken with food are combined into a third pill. 1504 illustrates determining the best way to label the pills. For example, color coding can be used. For example, an orange pill (or capsule) to be taken with food. A blue pill to be taken with water. Other color-coding schemes can be used as well. 1505 illustrates manufacturing of the dose. For example, use 3D printing. A 3D printer can be equipped with a container of aspirin, a container of Lipitor and a container of hydrochlorothiazide. A combination pill of these three medicines can be created. In some embodiments, the combination can be inserted into a food item, such as chocolate pudding. If the person misses a dose, then the ratio of the medications can be altered accordingly.

Figure 16:
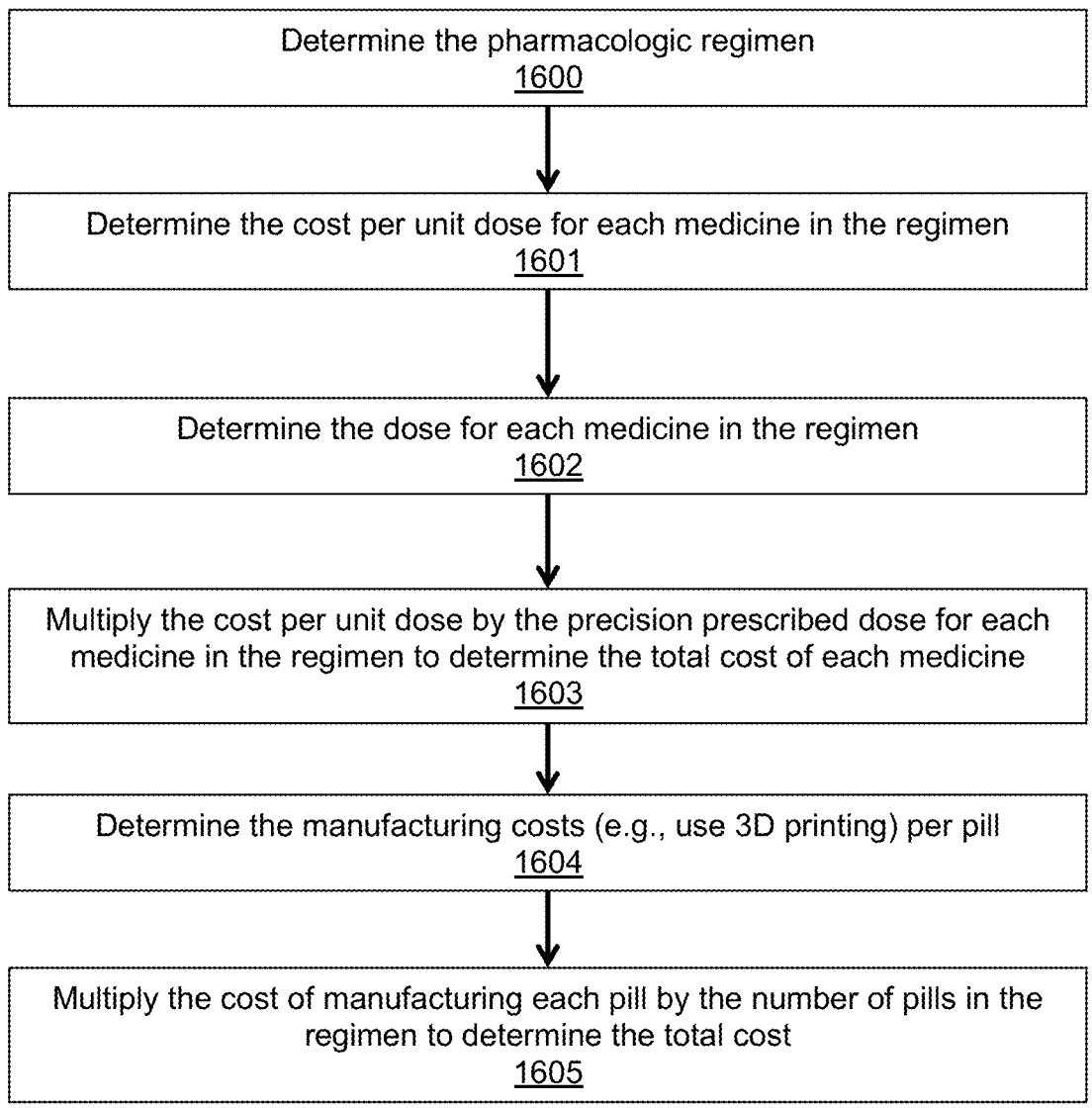
FIG. 16 illustrates a combination pill cost model.

FIG. 16 illustrates a combination pill cost model. 1600 illustrates determining the pharmacologic regimen. 1601 illustrates determining the cost per unit dose for each medicine in the regimen. 1602 illustrates determining the dose for each medicine in the regimen. 1603 illustrates multiplying the cost per unit dose by the precision prescribed dose for each medicine in the regimen to determine the total cost of each medicine. 1604 illustrates determining the manufacturing costs (e.g., use 3D printing) per pill. 1605 illustrates multiplying the cost of manufacturing each pill by the number of pills in the regimen to determine the total cost.

Figure 17:
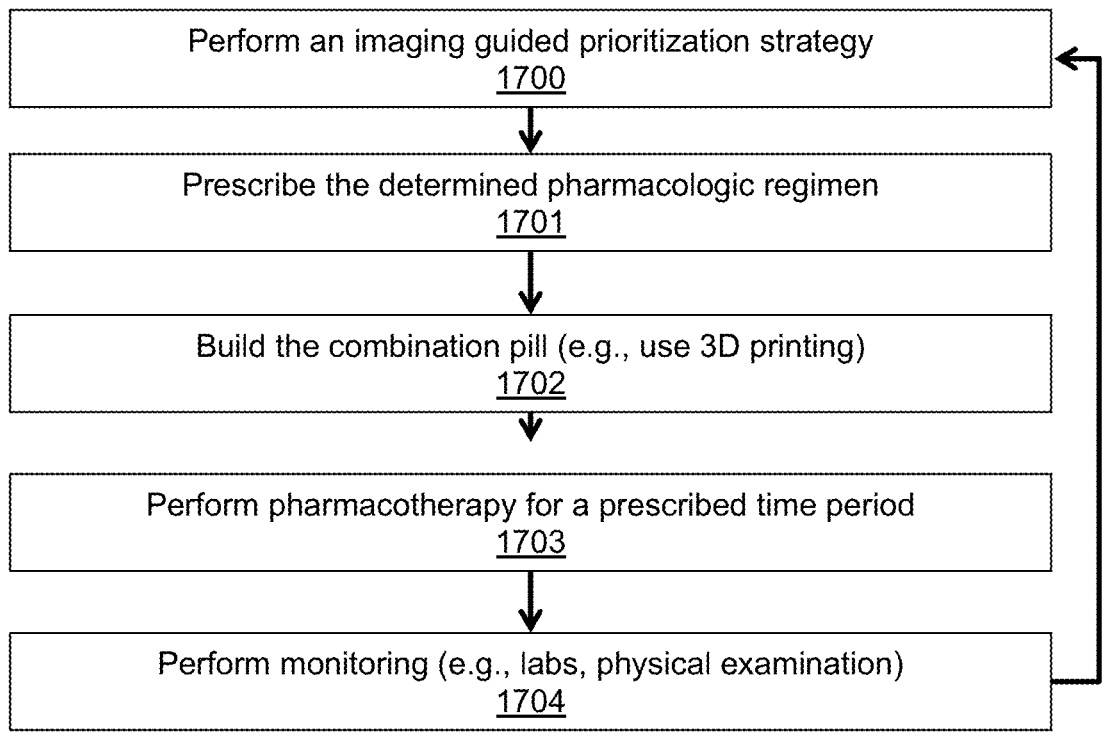
FIG. 17 illustrates a comprehensive care model.

FIG. 17 illustrates a comprehensive care model. 1700 illustrates performing an imaging guided prioritization strategy. 1701 illustrates prescribing the determined pharmacologic regimen. 1702 illustrates building the combination pill (e.g., use 3D printing). 1703 illustrates performing pharmacotherapy for a prescribed time period. 1704 illustrates perform monitoring (e.g., labs, physical examination).

Figure 18:
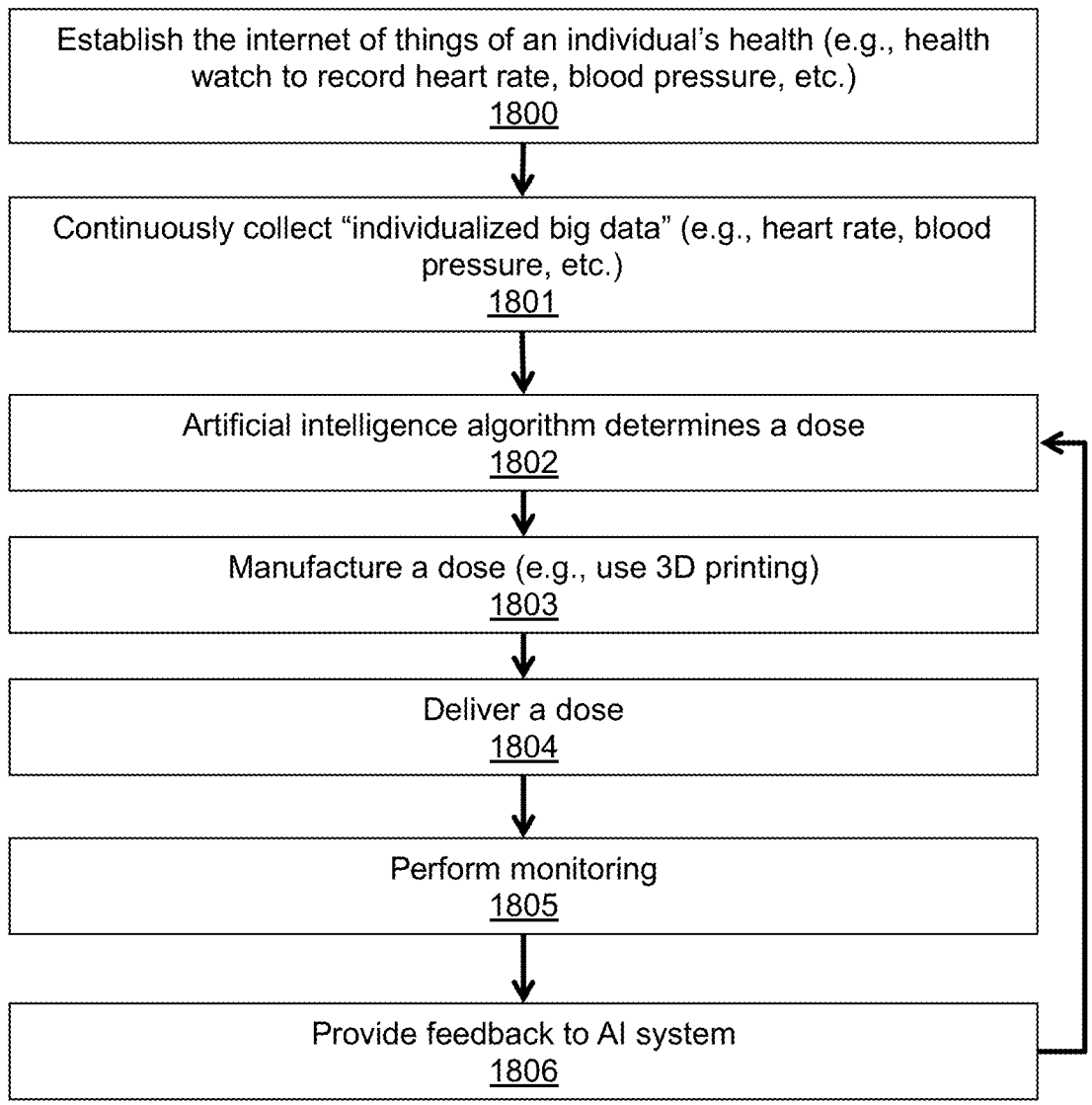
FIG. 18 illustrates utilizing "individualized big data" from the internet of things for precision pharmacotherapy and performing feedback for optimized wellness.

FIG. 18 illustrates utilizing "individualized big data" from the internet of things for precision pharmacotherapy and performing feedback for optimized wellness. 1800 illustrates establishing the internet of things of an individual's health (e.g., health watch to record heart rate, blood pressure, etc.) 1801 illustrates continuously collect "individualized big data" (e.g., heart rate, blood pressure, etc.). For example, an individual walked 20,000 steps in on Jul. 19, 2021, rather than the normal 10,000 steps per day. 1802 illustrates artificial intelligence algorithm determines a dose. 1803 illustrates manufacturing a dose. For example, a 3D printer can be used. Note that the dose delivered can be adjusted based on data from the internet of things. For example, given that the subject walked 20,000 steps on Jul. 19, 2021, the dosing strategy can be adjusted based on this and add an extra 1000 mg of calcium on Jul. 20, 2021, to help build up the bones. This would take advantage of the fact that the patient got an exceptional workout and would optimize rebuilding. Alternatively, if a person were stressed on 24 Dec. 2021 and this were identified (e.g., by poor sleeping patterns, changes in heart rate, questionnaire completed, voice changes), then the dose could be adjusted by adding a dose amount of St. John's Wort. The added dose of St. John's Wort could be adjusted based on imaging biomarkers. In some embodiments, the dose is mixed with a food item (e.g., via a 3D printer). 1804 illustrates delivering a dose. If a person were to have daily grocery delivery service, then the pills could be manufactured daily and delivered. Advanced delivery systems, such as using drones could also be performed. 1805 illustrates performing monitoring. Monitoring includes labs, physical examination and repeat imaging examinations for imaging biomarkers. 1806 illustrates providing feedback to AI system. Data from an individual includes number of steps; travel; calendar events; sleeping patterns; diet; stress level; workout level; study level; and social interactions. These data can be utilized to determine the dose of a pharmaceutical or combination of pharmaceuticals. For example, if the use is traveling on an international trip, a dose of Echinacea and zinc can be delivered as a prophylactic against acquiring an infection. For example, if the social interaction were a big speech in front of a large audience, then a dose of beta blocker can be delivered to ease stage fright. For example, if there is high level of stress (e.g., detected voice on cell phone), then a dose of St. John's Wort can be administered. If there is a significant workout, then additional calcium can be administered to help build bone strength. For example, if there is a big study day coming up, then a small dose of caffeine can be delivered. Thus, daily life events can be matched to pharmacologic therapy. These can be combined in a dose most closely matched to an individual patient. For example, Joe and Mary have a similar set of health conditions, but Joe's body analysis causes the dose received of calcium to be 1029 mg and Mary's body analysis causes the dose received of calcium to be 316 mg. Therefore, doses are individualized and matched to at least one of the group consisting of: individual's health parameters (labs, physical examination, vitals, weight); imaging biomarkers; and, daily activities (collected via the internet of things).

Figure 19:
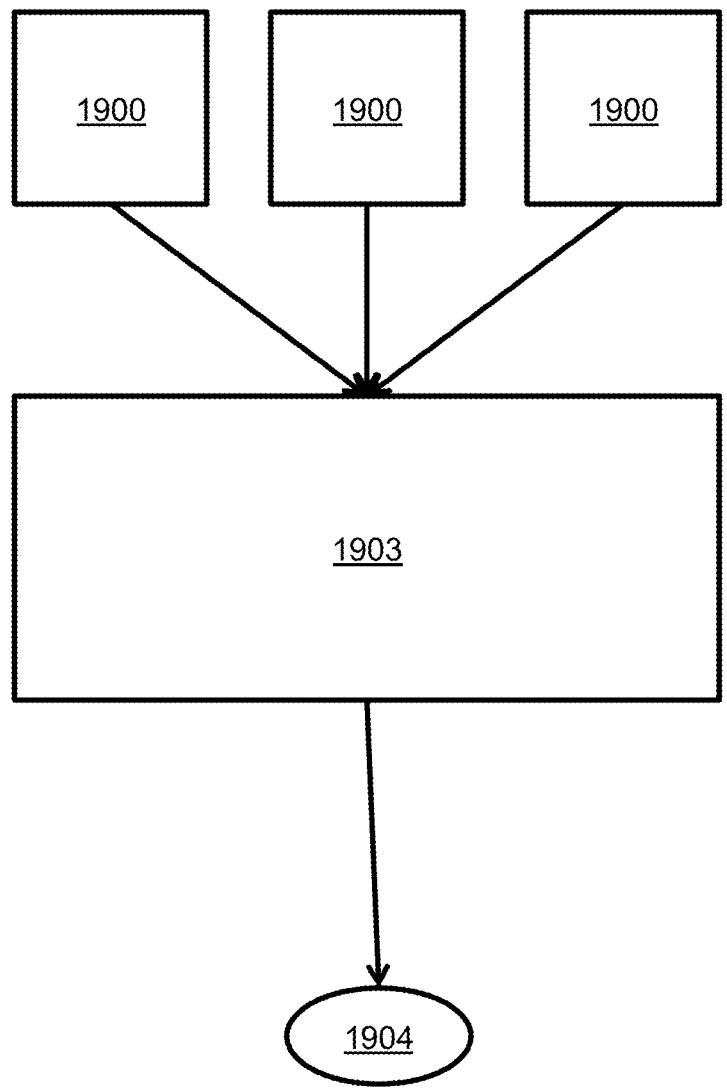
FIG. 19 illustrates manufacturing a combination pill.

FIG. 19 illustrates manufacturing a combination pill. 1900 illustrates a first drug in a first container. In this example, the first drug is aspirin. 1901 illustrates a second drug in a second container. In this example, the second drug is St. John's Wort. 1902 illustrates a third drug in a third container. In this example, the third drug is calcium. 1903 illustrates a 3D printer. Note that other method of combining the medications into a patient specific dose can be performed. The algorithm described in this patent is applied. The patient walked only 1000 steps the previous day so is scheduled to get a low dose of 421 mg calcium. The patient is getting ready for the in laws to visit for the holidays and is experiencing additional stress, so is scheduled to get 320 mg of St. John's Wort. The patient also is scheduled to get 103 mg of Aspirin. The 3D printer 1903 combines 103 mg of Aspirin from the first container 1900 and 320 mg of St. John's Wort from the second container 1901 and 421 mg of Calcium from the third container 1902 into a combination pill 1904. As described, at least three medications are utilized in this combination pill. However, other embodiments include one medicine, two medicines, or more than three medicines. Thus, in some embodiments, the activities of daily living can be factored into a pharmacologic dose.

Figure 20:
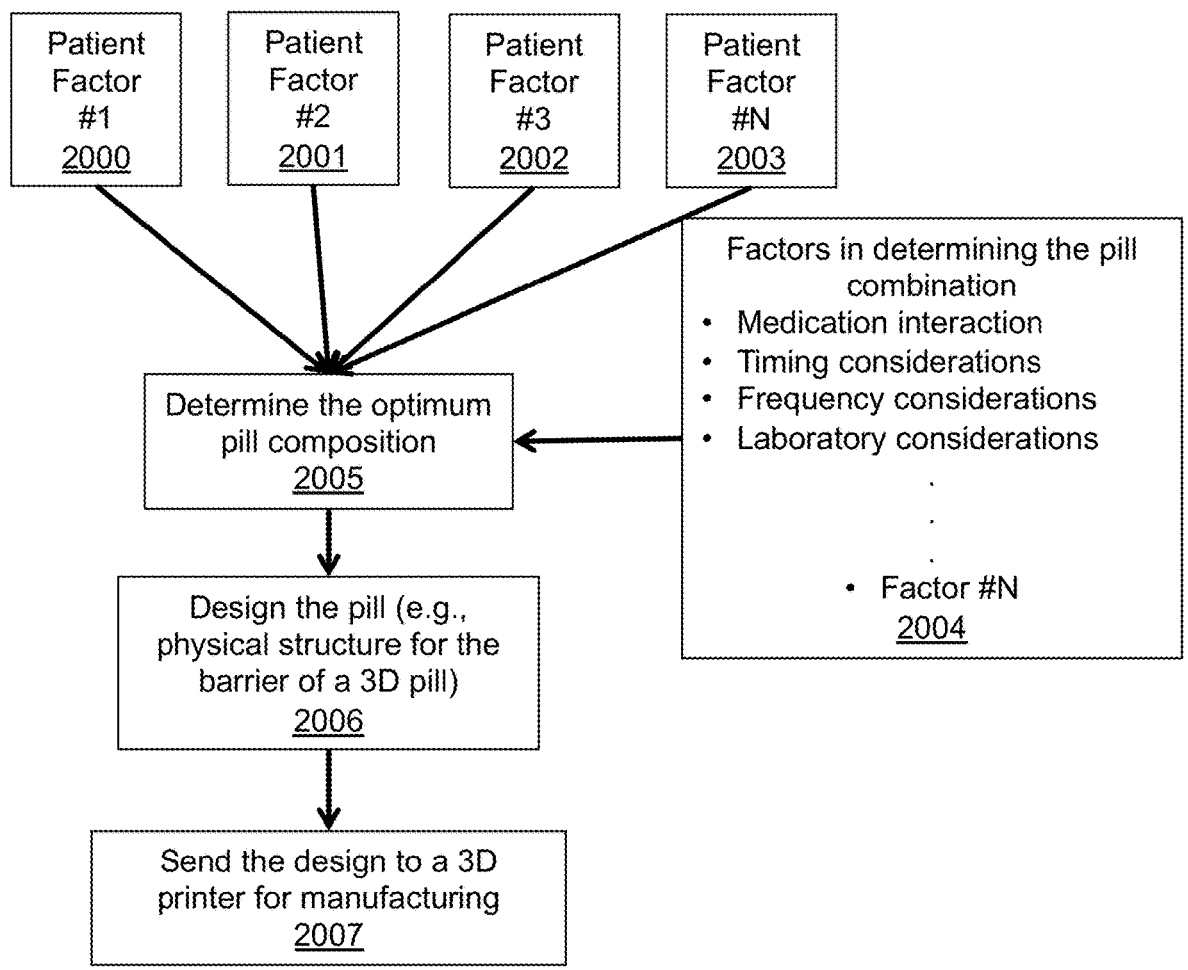
FIG. 20 illustrates a flow diagram for manufacturing a multi-drug combination pill.

FIG. 20 illustrates a flow diagram for manufacturing a multi-drug combination pill. Multiple patient factors (e.g., patient weight, body mass index, age, gender, co-morbidities, genetic factors, disease state, etc.) can be used to determine the optimum pill combination. 2000 illustrates patient factor #1. 2001 illustrates patient factor #2. 2002 illustrates patient factor #3. 2003 illustrates patient factor #N. 2004 illustrates factors in determining the pill combination, which include but are not limited to the following: medication interactions; timing considerations; frequency considerations; and, laboratory considerations. 2005 illustrates the determining the optimum pill combination. This could include what combination of drugs. This will be discussed more in FIGS. 21-23. 2006 illustrates designing the pill. For example, a multi-compartment design is preferred with dividers. The divider can vary in thickness and/or material to optimize release timing. For example, a thicker divider can have a slow release. A thin divider can have a fast release. Each drug can have a specific release time. For example, determine the optimum time of release of a first drug. And, determine the optimum time of release of a second drug. Then, design the physical structure for the pill. Note that patient preferences can be integrated. For example, some patients may want to take a pill in a capsule form whereas others may prefer a tablet form. This design is sent to a 3D printer for manufacturing 2007.

Figure 21A:
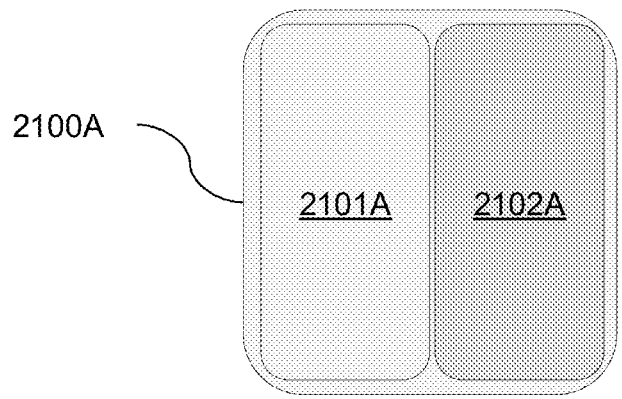

FIG. 21A illustrates two types of medications in one pill wherein there is no interaction between the two medications. A 3D printed pill 2100A is shown. A first compartment 2101A contains a first medication. A second compartment 2012A contains a second medication. Note that the walls of the first compartment 2101B are equal in thickness as compared to the walls of the second compartment 2102B. A variety of edible materials could be used to create the boundary for the compartments. A preferred option is nanocellulose.

Figure 21B:
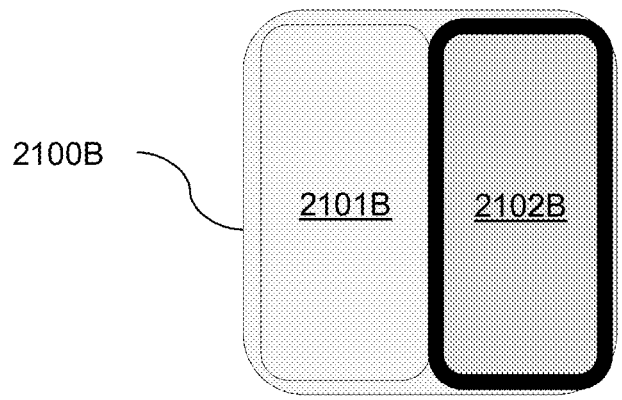

FIG. 21B illustrates two types of medications in one pill wherein there is an interaction between the two medications. A 3D printed pill 2100B is shown. A first compartment 2101B contains a first medication. A second compartment 2012B contains a second medication. Note that the walls of the first compartment 2101B are thinner than the walls of the second compartment 2102B. A variety of edible materials could be used to create the boundary for the compartments. A preferred option is nanocellulose.

Figure 21C:
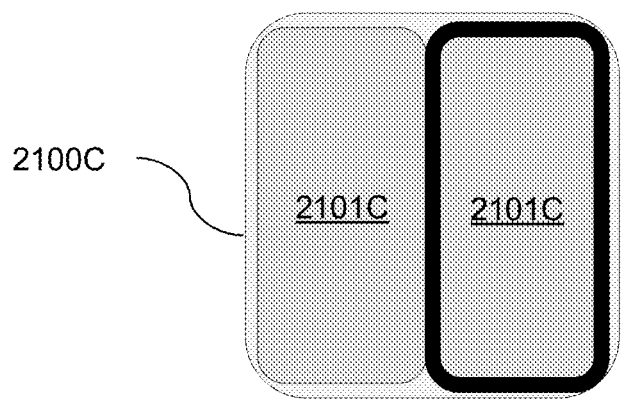

FIG. 21C illustrates one medication in one pill wherein the medication in the first compartment is released at a different time of day as compared to the medication in the second compartment. It should be noted that in this design, the multi-compartment pill 2100C is shown. The first compartment 2101C has walls of a first thickness. The second compartment 2102C has walls of a second thickness, which is thicker that the walls of the first compartment 2101C. This design is useful for twice daily dosing. For example, if a person was supposed to take Eliquis (Apixaban) twice daily dosing. The person could have a custom pill designed wherein the first dose of 5 mg of Eliquis is released shortly after swallowing the pill. Then, the second dose of 5 mg of Eliquis is released approximately 12 hours later. This would be useful because it would simplify dosing regimen. Note that the pill be designed in a way that is optimized for the user. For example, the size, shape, texture of the external surface, color of the external surface could be user-specified. For example, a husband may always choose to have red pills. A wife may always choose to take blue pills.

FIG. 22A illustrates a multi-compartment pill wherein there are three types of medications in one pill and wherein there is no interaction between any of the three medications. 2200A illustrates a multi-compartment, multi-drug pill, which contains a first medication in a first compartment 2201A, a second medication in a second compartment 2202A and a third medication in a third compartment 2203A. Note that since there is no interaction, the design could be a single compartment design. In this embodiment, the design is for three thin-walled compartments.

FIG. 22B illustrates a multi-compartment pill wherein there are three types of medications in one pill and wherein there is an interaction between one of the medications and the other two medications. 2200B illustrates a multi-compartment, multi-drug pill, which contains a first medication in a first compartment 2201B, a second medication in a second compartment 2202B and a third medication in a third compartment 2203B. Note that since there is an interaction, the design in this embodiment is to have a thick-walled compartment for the second compartment 2202B that interacts with the other two. Note the first compartment 2201B and the third compartment 2203B have thin walls.

FIG. 22C illustrates a multi-compartment pill wherein there are three types of medications in one pill and wherein all three medications interact. 2200C illustrates a multi-compartment, multi-drug pill, which contains a first medication in a first compartment 2201C, a second medication in a second compartment 2202C and a third medication in a third compartment 2203C. Note that since there is an interaction between all three medications, the design in this embodiment is to have a thin-wall for the first compartment 2201C, a thick-wall for the second compartment 2202C, and an extremely thick wall for the third compartment 2203C. This would allow deliver the first medication at a first time of day such as 8 AM, the second medication at a second time of day such as LOAM and a third medication at a third time of day such as 4 PM and would therefore be useful.

FIG. 23A illustrates a first pill with three medications with a first volume of a first medication, a second volume of a second medication, and a third volume of a third medication. 2300A illustrates the first pill, which contains a first volume of a first medication in a first compartment 2301A, a first volume of a second medication in a second compartment 2302A, and a first volume of a third medication in a third compartment 2303A. Note that in this example, volume in each compartment is equal.

FIG. 23B illustrates a second pill with three medications with different volumes of each medicine. 2300B illustrates the second pill, which contains a second volume of a first medication in a first compartment 2301B, a third volume of a second medication in a second compartment 2302B, and a second volume of a third medication in a third compartment 2303B. Note that in this example, the second volume in the first compartment 2301B is smaller than the first volume in the first compartment 2301A in FIG. 23A. Also, the second volume in the third compartment 2303B is smaller than the first volume in the third compartment 2303A in FIG. 23A. Also, the third volume in the second compartment 2302B is larger than the first volume in the second compartment 2302A in FIG. 23A. Note that a varying volume of medication based on dose adjustment techniques could be performed, such as adjusting the dose based on laboratory results.

FIG. 24A illustrates a first pill with three medications, each of which are stored in a compartment made of the same material. 2400A illustrates the first pill, which has a first compartment 2401A, a second compartment 2402A and a third compartment 2403A, each of which are made of the same material. A range of materials could be used. For example, various enteric coatings (polymer barrier, keratin, cellulose, shellac, plastics, waxes, fatty acids, etc.) could be used for the lining of the pill 2400A. This would help the pill traverse through the stomach and prevent any adverse events on the medications inside. A precise dosing regimen as described in this patent can be used to calculate the volume of each medication. The lining of each compartment in this example is made of the same material and the same thickness, so each medication would be released at approximately the same time.

FIG. 24B illustrates a second pill with three medications wherein compartments made of different materials. 2400B illustrates a second pill which has a first compartment 2401B made whose lining is made of a first material, a second compartment 2402B whose lining is made of a second material (different from the first material) and a third compartment 2403B whose lining is made of the first material.

Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein. The device(s) or computer systems that integrate with the processor(s) may include, for example, a personal computer (s), workstation(s) (e.g., Sun, HP), personal digital assistant (s) (PDA(s)), handheld device(s) such as cellular telephone (s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein. Although the methods and systems have been described relative to a specific embodiment thereof, they are not so limited. Obviously, many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

CLAIMS: Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
    looking up a first dose of a first medication;
    looking up a second dose of a second medication wherein said second medication is different from said first medication;
    analyzing an imaging examination of a user to determine at least one imaging biomarker
        wherein said at least one imaging biomarker is based on at least one segmented structure in said imaging examination;
    using said at least one imaging biomarker based on said at least one segmented structure and a set of patient factors of said user to determine an individualized first dose of said first medication and an individualized second dose of said second medication
        wherein said individualized first dose of said first medication is determined based on using said at least one imaging biomarker based on said at least one segmented structure and said set of patient factors of said user to adjust said first dose of said first medication into said individualized first dose of said first medication,
        wherein said individualized first dose of said first medication is different from said first dose of said first medication,
        wherein said individualized second dose of said second medication is determined based on using said at least one imaging biomarker based on said at least one segmented structure and said set of patient factors of said user to adjust said second dose of said second medication into said individualized second dose of said second medication, and
        wherein said individualized second dose of said second medication is different from said second dose of said second medication;
    designing a pill wherein said pill contains said individualized first dose of said first medication and said individualized second dose of said second medication; and,
    manufacturing said pill using a 3D printer.

2. The method of claim 1 further comprising wherein said set of patient factors comprises at least one of the group consisting of:
    a weight of a patient;
    a patient's gender;
    a patient's age;
    a patient's laboratory data;
    a patient's body mass index; and
    a patient's diagnosis.

3. The method of claim 2 further comprising wherein said individualized first dose of said first medication and said individualized second dose of said second medication are determined by an analysis of said at least one imaging biomarker based on said at least one segmented structure by an artificial intelligence algorithm.

4. The method of claim 3 further comprising wherein said pill comprises a first compartment and a second compartment wherein said first compartment and said second compartment are different compartments.

5. The method of claim 4 further comprising wherein said first compartment contains said first medication and said second compartment contains said first medication.

6. The method of claim 5 further comprising:
placing a first portion of said first individualized dose of said first medication in said first compartment wherein said first portion of said first individualized dose of said first medication is released from said first compartment into said user's gastrointestinal tract during a first time period; and
placing a second portion of said individualized first dose of said first medication in said second compartment wherein said second portion of said first individualized dose of said first medication is released from said second compartment into said user's gastrointestinal tract during a second time period wherein said second time period begins after said first time period.

7. The method of claim 4 further comprising wherein said first compartment contains said first medication and said second compartment contains said second medication.

8. The method of claim 7 further comprising:
wherein when said first medication is known to interact with said second medication, placing said first medication in said first compartment wherein said first medication is released from said first compartment into said user's gastrointestinal tract during a first time period; and
placing said second medication in said second compartment wherein said second medication is released from said second compartment into said user's gastrointestinal tract during a second time period wherein said second time period begins after said first time period.

9. The method of claim 4 further comprising:
wherein after said pill is swallowed by said user, said first compartment delivers its contents into a gastrointestinal tract of said user over a first time period;
wherein said second compartment delivers its contents into said gastrointestinal tract of said user over a second time period; and
wherein said first time period is different from said second time period.

10. The method of claim 4 further comprising:
wherein said first compartment's lining is of a made of a first material and said second compartment's lining is made of a second material;
wherein said first material is different from said second material; and
wherein said first material dissolves quicker in a gastrointestinal track as compared to said second material.

11. The method of claim 4 further comprising:
wherein said first compartments's lining is thicker than said second compartment's lining; and
wherein said first medication is released in a gastrointestinal track slower than said second medication.

12. The method of claim 4 further comprising:
wherein said first compartment is a first shape and said second compartment is a second shape; and
wherein said first shape is different from said second shape.

13. The method of claim 4 further comprising:
wherein said first compartment is contains a first volume and said second compartment contains a second volume; and
wherein said first volume is larger than said second volume.

14. The method of claim 4 further comprising:
wherein said first compartment is in a first position within said pill and said second compartment is in a second position within said pill; and
wherein said first position is different from said second position.

15. The method of claim 4 further comprising wherein said pill contains a third dose of a third medication and wherein said third dose is selected based on said user's preference.

16. The method of claim 4 further comprising wherein said pill is integrated into an edible item printed on said 3D printer and wherein said edible materials are selected based on said user's preference.

17. The method of claim 4 further comprising wherein said pill contains user selected vitamins and minerals.

18. An apparatus comprising:
a 3D printer wherein said 3D printer is configured to manufacture a pill
wherein a first dose of a first medication is determined;
wherein a second dose of a second medication is determined;
wherein said second medication is different from said first medication;
wherein an imaging examination of a user is analyzed to determine at least one imaging biomarker;
wherein said at least one imaging biomarker is based on at least one segmented structure in said imaging examination;
wherein said at least one imaging biomarker based on said at least one segmented structure and a set of patient factors of said user are used to determine an individualized first dose of said first medication and an individualized second dose of said second medication;
wherein said individualized first dose of said first medication is determined based on using said at least one imaging biomarker based on said at least one segmented structure and said set of patient factors of said user to adjust said first dose of said first medication into said individualized first dose of said first medication,
wherein said individualized first dose of said first medication is different from said first dose of said first medication,
wherein said individualized second dose of said second medication is determined based on using said at least one imaging biomarker based on said at least one segmented structure and said set of patient factors of said user to adjust said second dose of said second medication into said individualized second dose of said second medication,
wherein said individualized second dose of said second medication is different from said second dose of said second medication; and
wherein said pill contains said individualized first dose of said first medication and said individualized second dose of said second medication.

19. A non-transitory computer readable medium having computer readable code thereon for designing a pill, the medium comprising:
- instructions for looking up a first dose of a first medication;
- instructions for looking up a second dose of a second medication wherein said second medication is different from said first medication;
- instructions for analyzing an imaging examination of a user to determine at least one imaging biomarker wherein said at least one imaging biomarker is based on at least one segmented structure in said imaging examination;
- instructions for using said at least one imaging biomarker based on said at least one segmented structure and a set of patient factors of a user to determine an individualized first dose of said first medication and an individualized second dose of said second medication
  - wherein said individualized first dose of said first medication is determined based on using said at least one imaging biomarker based on said at least one segmented structure and said set of patient factors of said user to adjust said first dose of said first medication into said individualized first dose of said first medication,
  - wherein said individualized first dose of said first medication is different from said first dose of said first medication,
  - wherein said individualized second dose of said second medication is determined based on using said at least one imaging biomarker based on said at least one segmented structure and said set of patient factors of said user to adjust said second dose of said second medication into said individualized second dose of said second medication, and
  - wherein said individualized second dose of said second medication is different from said second dose of said second medication; and
- instructions for designing a pill wherein said pill contains said individualized first dose of said first medication and said individualized second dose of said second medication.

20. The medium of claim 19 further comprising wherein said pill comprises a first compartment containing said individualized first dose of said first medication and a second compartment containing said individualized second dose of said second medication wherein said first compartment and said second compartment are different compartments.

\* \* \* \* \*